(12) United States Patent
Minnelli et al.

(10) Patent No.: US 10,136,939 B2
(45) Date of Patent: Nov. 27, 2018

(54) ENERGY DELIVERY DEVICE HAVING A TRANSLATING OUTER SHEATH

(71) Applicant: Ethicon LLC, Guaynabo, PR (US)

(72) Inventors: Patrick J. Minnelli, Harrison, OH (US); Adam Brown, Lebanon, OH (US); Terry McFarland, Burlington, KY (US)

(73) Assignee: Ethicon LLC, Guaynabo, PR (US)

( * ) Notice: Subject to any disclaimer, the term of this patent is extended or adjusted under 35 U.S.C. 154(b) by 898 days.

(21) Appl. No.: 14/547,882

(22) Filed: Nov. 19, 2014

(65) Prior Publication Data
US 2016/0135872 A1 May 19, 2016

(51) Int. Cl.
*A61B 1/00* (2006.01)
*A61B 18/14* (2006.01)
(Continued)

(52) U.S. Cl.
CPC ...... *A61B 18/1445* (2013.01); *A61B 17/2909* (2013.01); *A61B 17/320016* (2013.01); *A61B 18/1206* (2013.01); *A61B 18/1482* (2013.01); *A61B 2017/0038* (2013.01); *A61B 2017/0042* (2013.01); *A61B 2017/00336* (2013.01); *A61B 2017/00371* (2013.01); *A61B 2017/00376* (2013.01); *A61B 2017/00384* (2013.01); *A61B 2017/00424* (2013.01); *A61B 2017/00438* (2013.01); *A61B 2017/2916* (2013.01); *A61B 2017/2922* (2013.01); *A61B 2018/0094* (2013.01); *A61B 2018/00196* (2013.01);
(Continued)

(58) Field of Classification Search
CPC .................. A61B 18/1445; A61B 17/2909
USPC .......................................................... 606/45
See application file for complete search history.

(56) References Cited

U.S. PATENT DOCUMENTS

| 5,197,963 A | * | 3/1993 | Parins | ............... A61B 18/1482 |
| | | | | 606/41 |
| 9,468,454 B2 | * | 10/2016 | Johnson | ........... A61B 17/32002 |

FOREIGN PATENT DOCUMENTS

| EP | 0545540 A1 | 6/1993 |
| WO | WO-9944509 A1 | 9/1999 |

OTHER PUBLICATIONS

Ethicon Endopath Electrosurgery Probe Plus II. <http://www.ethicon.com/healthcare-professionals/products/other/electrosurgical-irrigation> retrieved on Aug. 18, 2018.

(Continued)

*Primary Examiner* — Nadia A Mahmood
(74) *Attorney, Agent, or Firm* — Mintz Levin Cohn Ferris Glovsky and Popeo, P.C.

(57) ABSTRACT

Devices and methods for applying energy to tissue are provided. In one exemplary embodiment, a surgical device includes a monopolar end effector, a cannulated, insulated outer sheath, a translating nozzle coupled to the proximal end of the sheath, and a handle portion coupled to a proximal end of the end effector. Various translating means, such as switches, thumbwheels, rings, and buttons, are associated with the handle portion, and are effective to advance the outer sheath to cover a distal end of the end effector and retract the outer sheath to expose the distal end of the end effector. The translating means are configured in a manner that allows a user to operate the translating means without having to adjust a location of the user's hand on the device. A variety of translating means are provided for, as are methods for cutting, coagulating, irrigating, and suctioning tissue.

20 Claims, 17 Drawing Sheets

(51) Int. Cl.
*A61B 18/12* (2006.01)
*A61B 17/29* (2006.01)
*A61B 17/32* (2006.01)
*A61B 17/00* (2006.01)
*A61B 18/00* (2006.01)
*H01H 9/06* (2006.01)

(52) U.S. Cl.
CPC ............... *A61B 2018/00589* (2013.01); *A61B 2018/00595* (2013.01); *A61B 2018/00601* (2013.01); *A61B 2018/00922* (2013.01); *A61B 2018/00958* (2013.01); *A61B 2018/126* (2013.01); *A61B 2018/1253* (2013.01); *A61B 2018/1422* (2013.01); *A61B 2018/1475* (2013.01); *A61B 2217/005* (2013.01); *A61B 2217/007* (2013.01); *A61B 2218/002* (2013.01); *A61B 2218/007* (2013.01); *H01H 9/06* (2013.01); *H01H 2300/014* (2013.01)

(56) References Cited

OTHER PUBLICATIONS

International Search Report and Written Opinion for Application No. PCT/US2015/061452 dated May 30, 2016.
[No Author Listed] "Endopath® Probe Plus II, Multi-Function Electrosurgery System," product information sheet; 2 pages, 2010.

* cited by examiner

ENERGY DELIVERY DEVICE HAVING A TRANSLATING OUTER SHEATH

FIELD

The present invention relates to an energy delivery device used for cutting or coagulating, and more particularly to an energy delivery device that includes a translating outer sheath to selectively expose and cover a distal end of an energy delivery end effector of the device.

BACKGROUND

Surgical devices are used in various open, endoscopic, and laparoscopic surgeries to transect or coagulate tissue at a surgical site. The devices generally include a handle portion that is gripped by the surgeon using the device, an energy delivery end effector that delivers energy to the surgical site to perform the transection (i.e., cutting) or coagulation, and an outer sheath disposed around the energy delivery end effector so that a distal end of the energy delivery end effector can be selectively exposed and covered during the delivery and use of the surgical device. One exemplary embodiment of such a device is the Endopath® Probe Plus II, manufactured by Ethicon-Endo Surgery, Inc. of Cincinnati, Ohio.

Existing transection and coagulation devices, however, can be improved to enhance the user experience. For example, in existing embodiments of transection and coagulation devices, deploying the outer sheath to either expose the distal end of the end effector or cover the distal end of the end effector can be cumbersome. In some instances, a surgeon may use a second hand to manually move the outer sheath proximally, i.e., towards the surgeon, to expose the distal end of the end effector or distally, i.e., away from the surgeon, to cover the distal end of the end effector. In other instances a surgeon may move his or her hand from its initial location to use one or more fingers to initiate the distal or proximal movement of the outer sheath. For example, a surgeon often moves their his or her hand away from a pistol grip position, which can be used to initially guide the surgical device to the surgical site, to more of a palming grip that allows the surgeon to keep the surgical device relatively in the same location while using his or her index or middle finger to advance or retract the outer sheath. Once the sheath has been adjusted as desired, the surgeon then returns his or her hand to the pistol grip position to operate various features of the device, such as transecting, coagulating, vacuuming, or irrigating functions. Because the sheath is generally refracted when transecting or coagulating, and extended when vacuuming or irrigating, the surgeon often adjusts his or her grip a number of times during the course of a surgical procedure in order to keep exposing or covering the distal end of the end effector. In addition to this back-and-forth switching between grips being inconvenient, each time the grip change is made, the device may be jostled, thereby causing unintentional damage to surrounding tissue and the like or causing the device to stray from the intended surgical site.

Accordingly, there remains a need for improved surgical devices that allow a user to utilize a single grip on a surgical device during the course of a surgical procedure to transect or coagulate tissue.

SUMMARY

Devices and methods are generally provided for enhanced surgical devices designed to transect (i.e., cut) or coagulate tissue. The designs provided for herein allow a surgeon to maintain a single grip on the surgical device while using the gripping hand to position the device at the surgical site, selectively expose and cover a distal end of an energy delivery end effector of the device, and operate the device to perform the transection and/or coagulation. In one exemplary embodiment, a surgical device includes an end effector, a cannulated outer sheath, a translating nozzle, and a handle portion. The end effector has a proximal end, a distal end, and an elongate shaft extending between the proximal and distal ends. The distal end of the end effector can be configured to delivery energy. In some embodiments, the end effector can be monopolar.

The cannulated outer sheath has a proximal end, a distal end, and an intermediate length extending between the proximal and distal ends. The end effector is disposed within the outer sheath. In some embodiments, the distal end of the outer sheath can have a plurality of holes formed in an outer surface of the sheath. The holes can be in fluid communication with the remainder of the cannulated outer sheath to provide at least one of suction and irrigation to a surgical site. Thus, the holes can be in fluid communication with a fluid source and/or a vacuum source. Further, in some embodiments, the outer sheath can include an insulating material that is configured to insulate the monopolar end effector when the outer sheath is distally advanced to cover the distal end of the end effector.

The translating nozzle is coupled to the proximal end of the outer sheath and is configured to translate along a longitudinal axis of the cannulated outer sheath. The handle portion is coupled to the proximal end of the end effector. Further, the handle portion includes a switch that is operatively coupled to the nozzle. The switch is effective to both distally advance the nozzle with respect to the handle portion to selectively cover the distal end of the end effector with the distal end of the outer sheath, and proximally retract the nozzle with respect to the handle portion to selectively expose the distal end of the end effector. In some embodiments, the switch can be configured to selectively apply energy to the end effector.

In one exemplary embodiment of a switch, the switch can include a carrier that is coupled to the nozzle and a plurality of segments, including a distal-most segment and a proximal-most segment. The distal-most segment can be coupled to the carrier, and a proximal end of the proximal-most segment can extend proximally away from a back end of the handle portion. The switch can be configured to distally advance the nozzle with respect to the handle portion in response to an extension force applied to the proximal-most segment in a direction substantially perpendicular to the longitudinal axis of the outer sheath. Likewise, the switch can be configured to proximally retract the nozzle with respect to the handle portion in response to a refraction force applied to the proximal-most segment in a direction approximately opposite to the direction of the extension force.

In another exemplary embodiment of a switch, the switch can include a carrier that is coupled to the nozzle and a plurality of linkages, including two distal-most linkages and a proximal-most linkage. The two distal-most linkages can be coupled to opposed sides of the carrier, a proximal end of the proximal-most linkage can extend outside of a housing of the handle portion, and the proximal-most linkage can be configured to rotate about a pivot point of the plurality of linkages. The switch can be configured to distally advance the nozzle with respect to the handle portion in response to an extension force applied to the proximal-most linkage to rotate the proximal-most linkage about the pivot point in a first direction. Likewise, the switch can be configured to proximally retract the nozzle with respect to the handle portion in response to a retraction force applied to the proximal-most linkage to rotate the proximal-most linkage about the pivot point in a second direction that is opposite of the first direction.

In still another exemplary embodiment of a switch, the switch can include a carrier that is coupled to the nozzle and a translating arm. The carrier can have a tab that is disposed on a proximal portion of the carrier. The translating arm can have a distal end that is rotatably coupled to a housing of the handle, an intermediate portion that includes an elongate channel formed therein, and a proximal end extending outside of a housing of the handle portion. The tab of the carrier can be disposed in the elongate channel so it can translate within the channel. The switch can be configured to distally advance the nozzle with respect to the handle portion in response to an extension force applied to the proximal end of the translating arm in a direction substantially perpendicular to the longitudinal axis of the outer sheath. Likewise, the switch can be configured to proximally retract the nozzle with respect to the handle portion in response to a retraction force applied to the proximal end of the translating arm in a direction approximately opposite to the direction of the extension force.

In yet another exemplary embodiment of a switch, the switch can include a carrier that is coupled to the nozzle and a slider. The carrier can have a tab that is disposed on a proximal portion of the carrier. The slider can have an elongate channel formed therein and first and second arms disposed on opposed sides of an intermediate portion of the length of the elongate channel. The elongate channel can be disposed at an angle with respect to the longitudinal axis of the outer sheath such that an angle extending between a distal end of the elongate channel and the longitudinal axis of the outer sheath is an acute angle. The tab of the carrier can be disposed in the elongate channel so it can translate within the channel. The switch can be configured to distally advance the nozzle with respect to the handle portion in response to an extension force applied to the first arm in a direction substantially perpendicular to the longitudinal axis of the outer sheath. Likewise, the switch can be configured to proximally retract the nozzle with respect to the handle portion in response to a retraction force applied to the second arm in a direction approximately opposite to the direction of the extension force.

In another exemplary embodiment of a switch, the switch can include a carrier that is coupled to the nozzle and a slide tab coupled to a proximal end of the carrier. The slider tab can extend outside of a top end of the handle portion. The switch can be configured to distally advance the nozzle with respect to the handle portion in response to an extension force applied to the slider tab in a direction substantially parallel to the longitudinal axis of the outer sheath. Likewise, the switch can be configured to proximally retract the nozzle with respect to the handle portion in response to a retraction force applied to the slider tab in a direction approximately opposite to the direction of the extension force.

In another exemplary embodiment of a surgical device, the device includes a handle portion, an end effector extending distally from the handle portion, an outer sheath that also extends distally from the handle portion, and a translating means. The end effector has a distal end that is configured to delivery energy. The outer sheath has a through-hole extending its length, and the end effector is disposed in the outer sheath. Further, the outer sheath is configured to distally advance and proximally retract to selectively cover and expose the distal end of the end effector. The translating means is for distally advancing and proximally retracting the outer sheath with respect to the distal end of the end effector. The translating means is associated with the handle portion, and it is configured to be operated to advance or retract the outer sheath with a user's hand disposed on the handle portion without the user having to adjust a location of the user's hand from a location at which the hand is disposed when positioning the device and applying energy to the end effector.

In some embodiments, the handle portion can include a pistol grip on which the user's hand is configured to be disposed when the user operates the translating means, positions the device, and applies energy to the end effector. The translating means can include at least one of a switch, a thumbwheel, a push-pull ring, and a button configured to both retract the outer sheath and apply energy to the end effector. In some embodiments, a nozzle can be coupled to both the outer sheath and the translating means. As a result, operation of the translating means can distally advance the nozzle to distally advance the outer sheath, and likewise can proximally retract the nozzle to proximally retract the outer sheath. The device can include a carrier that is disposed within and coupled to a housing of the nozzle. The carrier can be coupled to the translating means such that operation of the translating means distally advances the carrier to distally advance the nozzle, and likewise, can proximally retract the carrier to proximally retract the nozzle. In some embodiments, the translating means can be configured to selectively apply energy to the end effector.

One exemplary surgical method provided for herein begins by gripping a handle portion of a surgical device with a hand to establish a gripping position of the hand. The method further includes guiding an energy delivery end effector of the surgical device to a surgical site using the hand gripping the handle portion while the hand remains in the gripping position. The energy delivery end effector is disposed within an outer sheath of the surgical device. The method includes operating a switch with the hand gripping the handle portion to retract the outer sheath to expose a distal end of the energy delivery end effector. During this step, again the hand remains in the gripping position. Energy is applied to the energy delivery end effector, and subsequently, the application of the energy is ceased. The switch can be operated again with the hand gripping the handle portion, but this time to extend the outer sheath over the distal end of the energy delivery end effector. Again, the hand remains in the gripping position during this step. The method can further include guiding the energy delivery end effector away from the surgical site.

Applying energy to the energy delivery end effector can be effective to at least transect or coagulate tissue at a surgical site, or do both. In some embodiments, the method can also include irrigating the surgical site by passing fluid through the outer sheath while the outer sheath is extended over the distal end of the energy delivery end effector. In some other embodiments, the method can also include applying a vacuum force through the outer sheath to evacuate fluid from the surgical site while the outer sheath is extended over the distal end of the energy delivery end effector. The energy delivery end effector can include a monopolar electrode. In some embodiments, the step of applying energy to the energy delivery device can include operating the switch to apply the energy.

BRIEF DESCRIPTION OF DRAWINGS

This invention will be more fully understood from the following detailed description taken in conjunction with the accompanying drawings, in which.

DETAILED DESCRIPTION

Figure 1A:
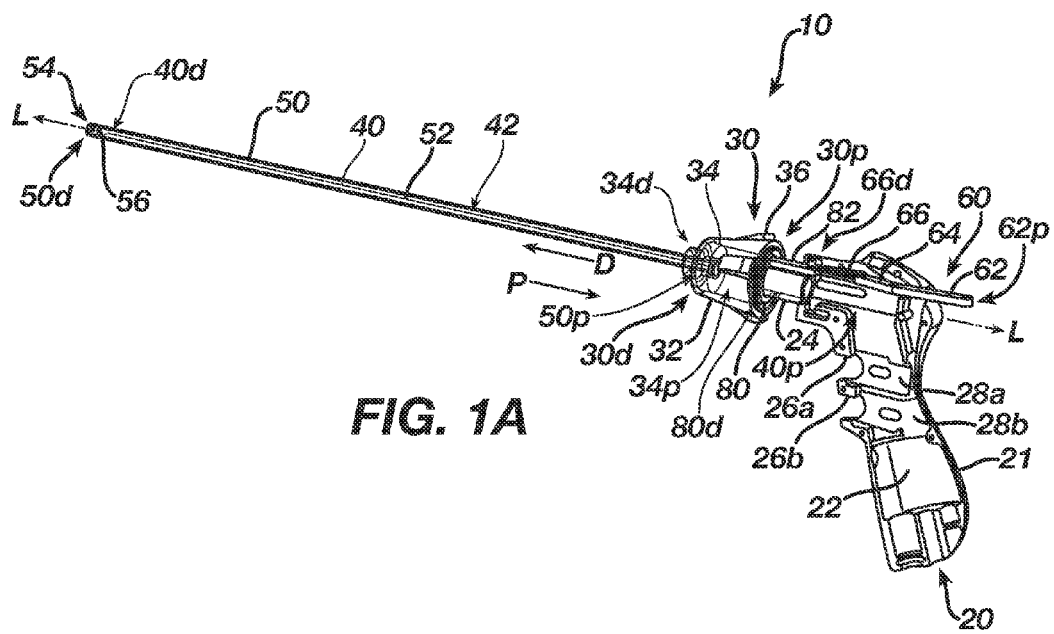
FIG. 1A is a semi-transparent perspective view of one exemplary embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose. Additionally, to the extent features, sides, or directions are described herein as being a "first feature" or "first direction" or a "second feature" or "second direction," such numerical ordering is generally arbitrary, and thus such numbering can be interchangeable.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Additionally, to the extent terms for applying a force to a component are described as involving "pushing" or "pulling," a person skilled in the art will recognize that actions such as pushing or pulling can typically be performed interchangeably without departing from the spirit of the present disclosure.

The present disclosure generally relates to surgical devices and methods for selectively covering and exposing a distal end of an energy delivery end effector with an outer sheath during the course of a surgery that involves transecting (i.e., cutting) or coagulating tissue with the end effector. More particularly, a variety of different mechanisms that are associated with a handle portion of the surgical device and are configured to actuate the outer sheath distally and proximally are provided for herein. The mechanisms, also referred to as translating means, allow a surgeon to maintain a single grip on the handle portion throughout the course of a surgical procedure. As a result, the surgeon can hold the handle portion in one hand and maintain the same grip while moving an outer sheath of the device over or away from the distal end of the energy delivery end effector, applying energy to the end effector or performing other tasks the device is configured to perform (e.g., providing irrigation and/or suction to the surgical site), and subsequently removing the device from the surgical site. The various embodiments of the translating means disclosed herein include a variety of switches, thumbwheels, rings, and buttons, as shown in FIGS. 1A, 1B, and 3A-18B, and each embodiment illustrated, described herein, or otherwise derivable from the present disclosures, represents an embodiment of the translating means.

Surgical Device

Figure 1B:
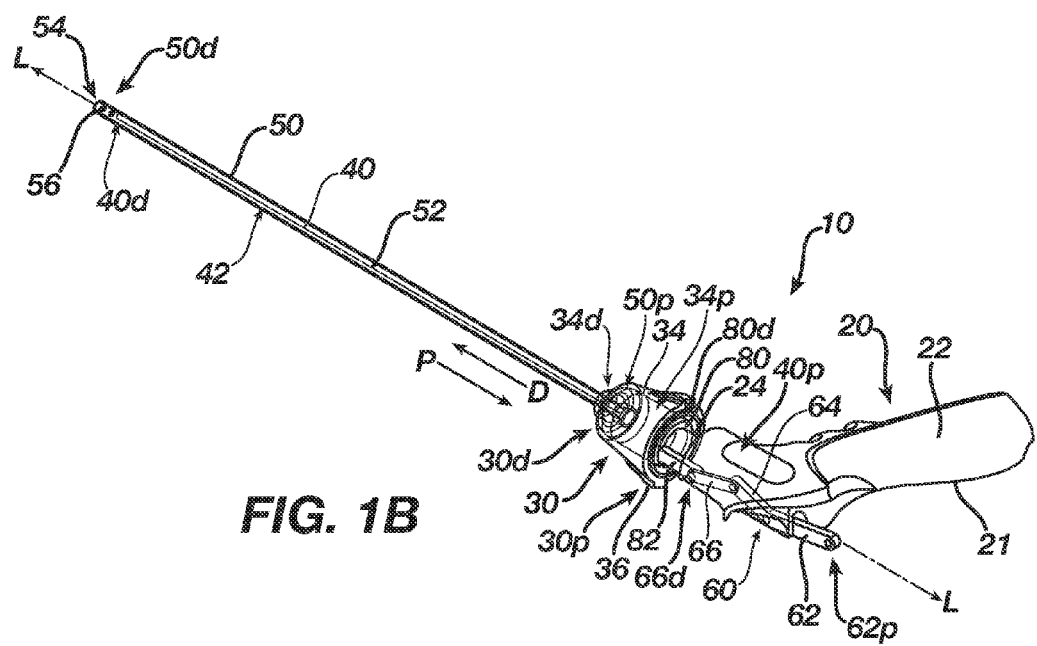
FIG. 1B is another semi-transparent perspective view of the surgical device of FIG. 1A.

FIGS. 1A and 1B illustrate one embodiment of a surgical device 10 configured to transect or cut and/or coagulate tissue. The device 10 can include a proximal handle portion 20, a nozzle 30, an end effector 40, and an outer sheath 50. In some instances, the nozzle 30 can be considered to be part of the handle portion, in which case the handle portion can include a proximal portion that includes a stationary handle and a distal portion that includes the nozzle 30. As shown, the end effector 40 and outer sheath 50 can both extend distally away from the handle portion 20, with a proximal end 40p of the end effector 40 being coupled to the handle portion 20 and a proximal end 50p of the outer sheath 50 being coupled to the nozzle 30. The nozzle 30 can be configured to translate both away from and towards the handle portion 20 along a longitudinal axis L that extends centrally through the outer sheath 50. As the nozzle 30 advances distally away from the handle portion 20, so too does the outer sheath 50. The handle portion 20 and end effector 40 remain stationary, and thus a distal end 50d of the outer sheath 50 can extend over a distal end 40d of the end effector 40 when the nozzle 30 advances distally to an extended position. Likewise, as the nozzle 30 retracts proximally towards the handle portion 20, so too does the outer sheath 50. Again, the handle portion 20 and end effector 40 remain stationary, and thus retraction of the nozzle 30 to a retracted position allows the outer sheath 50 to travel proximally to expose the distal end 40d of the end effector 40 for use to transect or coagulate tissue.

As shown, the outer sheath 50 is a cannulated or hollow generally elongate cylindrical tube. The tube includes a proximal end 50p, a distal end 50d, and an intermediate length extending between the proximal and distal ends 50p, 50d, with an opening 54 extending the entire length of the sheath 50. The proximal end 50p can be configured to couple to the nozzle 30 using any number of coupling techniques, including, by way of non-limiting examples, mechanical coupling techniques such as an interference fit, a snap-fit, and a threaded configuration. In some exemplary embodiments, engagement between the outer sheath 50 and the nozzle 30 allows the outer sheath 50 to be removably and replaceably coupled to the nozzle 30. A removable and replaceable sheath 50 allows differently sized, shaped, and configured sheaths to be mixed and matched with the other components of the device 10, which in turn provides a versatile array of performance options for the device.

The distal end 50d can include a plurality of holes 56 formed through an outer surface or wall 52 of the sheath 50. The holes 56 can be in fluid communication with a remaining portion of the length of the sheath 50 that extends proximally towards the handle portion 20, and also in fluid communication with components associated with the sheath 50 and/or the handle portion 20. The fluid communication allows a fluid or a vacuum force to be applied to the surgical site. For example, a fluid source or vacuum source (not shown) can be disposed in the handle portion 20, or disposed outside of the handle portion 20 and hooked up to the handle portion 20 or the outer sheath 50. A fluid or a vacuum force can then be supplied by way of the respective fluid or vacuum source, through the sheath 50, and out of the holes 56 to the surgical site. Any number of holes can be formed in the outer surface 52, and in some embodiments the number of holes is approximately in the range of about 0 holes to about 10 holes. In embodiments in which there are 0 holes formed, fluid and vacuum forces can be provided through the opening 54 that extends the length of the outer sheath 50.

While in the illustrated embodiment the outer sheath 50 is generally cylindrical, the outer sheath 50 can have any number of shapes, sizes, and configurations, depending, at least in part, on the sizes, shapes, and configurations of the other components of the device 10, the anatomy of the patient, and the type of procedure being performed. A length of the outer sheath 50 is selected so that it is long enough to cover the distal end 40d of the end effector 40 when the outer sheath 50 is in an extended position, and short enough to allow the distal end 40d to be exposed when the outer sheath 50 is in a retracted position. In some exemplary embodiments, a length of the outer sheath 50 is approximately in the range of about 20 centimeters to about 50 centimeters, and in one embodiment the length is about 35 centimeters. A diameter of the outer sheath 50 is selected so that the cannulated portion of the outer sheath 50 is large enough to receive the end effector 40 while still allowing for fluid to flow therethrough. In some exemplary embodiments, a diameter of the outer sheath 50 is approximately in the range of about 3 millimeters to about 12 millimeters, and in one embodiment the diameter is about 5 millimeters. When the outer sheath 50 is provided as part of a kit that provides multiple sheaths, the outer sheaths can have different lengths and diameters. By way of non-limiting example, in some kits some of the sheaths can have a diameter of about 5 millimeters, and other sheaths can have a diameter of about 10 millimeters.

Many different materials can be used to form the outer sheath 50. Typically, materials having insulating properties are used so that the energy delivering distal end 40d of the end effector 40 is insulated from the surgical site when irrigating. The material is also generally strong enough to protect tissue, organs, and the like in the body from being accidentally poked by the covered end effector 40 when passing the device 10 through the body, to and from the surgical site. Some examples of insulating materials that can be used to form the outer sheath include but are not limited to various plastics such as polyoxymethylene copolymer (POM), polyamides, polycarbonate, polyetherimide, polyetheretherketone, polyethylene, polylactic acid/polylactide acid (PLA), polypropylene, polystyrene, polyurethane, polyvinyl chloride (PVC), and thermoplastic elastomer. In one exemplary embodiment, the outer sheath is made from polyethylene.

As shown, the end effector 40 generally includes a proximal end 40p coupled to the handle portion 20, a distal end 40d proximate to the distal end 50d of the outer sheath 50 so that the distal end 40d can be selectively covered and exposed by the outer sheath 50, and an elongate length or shaft 42 extending between the proximal and distal ends 40p, 40d. The proximal end 40p can be in electrical communication with components in the handle portion 20 such that energy can be delivered through the shaft 42 and to the distal end 40d. In the illustrated embodiment, the end effector 40 is monopolar such that energy delivered travels from the end effector 40, to the tissue being treated, and then returns back through the end effector 40 to complete the path. In other embodiments, the end effector can be a bipolar configuration so that energy supplied to one electrode can pass from the electrode, through the tissue, and to a second, return electrode. One, non-limiting exemplary embodiment of a bipolar end effector that can be used in conjunction with the disclosures provided for herein includes devices disclosed in U.S. Ser. No. 14/166,133, entitled "Improved Motor Control and Feedback in Powered Surgical Devices," filed Jan. 28, 2014, and which is incorporated by reference herein in its entirety, and with any modifications to the other components of the device 10 (or other devices provided for herein) being necessary to operate with this bipolar end effector being within the skill of the art. Incorporating the disclosures in a bipolar end effector like the one referenced above can allow the outer sheath 50 to protect a blade of the device.

Figure 2A:
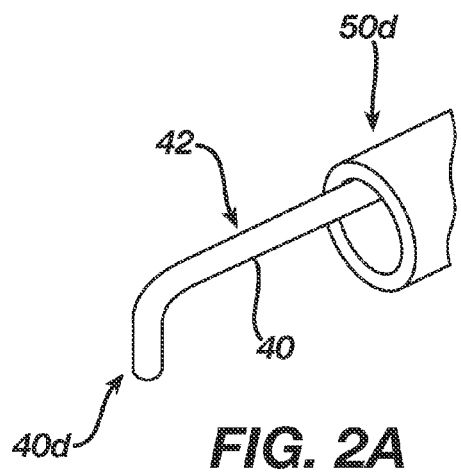
FIG. 2A is a perspective view of a distal end of an end effector of the surgical device of FIG. 1A.
Figure 2B:
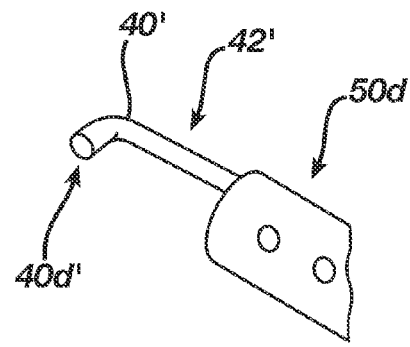
FIG. 2B is a perspective view of another exemplary embodiment of a distal end of an end effector that can be used with surgical devices such as the device of FIG. 1A.
Figure 2C:
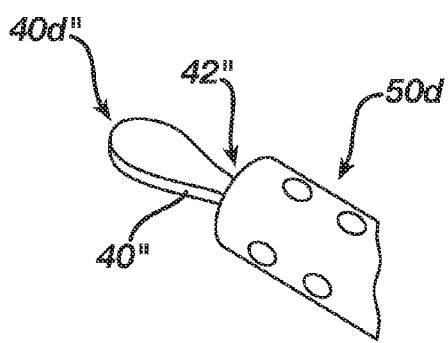
FIG. 2C is a perspective view of yet another exemplary embodiment of a distal end of an end effector that can be used with surgical devices such as the device of FIG. 1A.
Figure 2D:
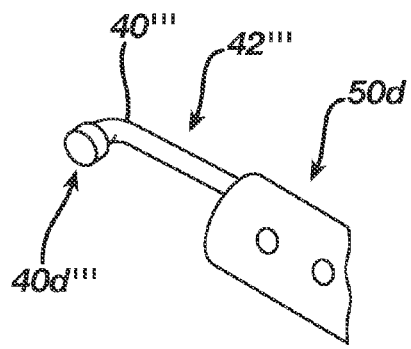
FIG. 2D is a perspective view of still another exemplary embodiment of a distal end of an end effector that can be used with surgical devices such as the device of FIG. 1A.

The distal end 40d of the end effector 40 can have a variety of configurations to transect and coagulate. Some exemplary embodiments of distal ends 40d are provided in FIGS. 2A-2D. The distal end 40d illustrated in FIG. 2A is disposed at approximately a right angle with respect to the shaft 42. The distal end 40d' of the end effector 40' illustrated in FIG. 2B is referred to as a hook, and thus curves away from the shaft 42' to form a more rounded configuration than the distal end 40d of FIG. 2A. The distal end 40d" of the end effector 40" illustrated in FIG. 2C is referred to as a spatula. As shown, the spatula configuration provides for a more cylindrical or rounded distal end, and does not contain the sharper bends that exist in the distal ends 40d, 40d' of FIGS. 2A and 2B. The spatula is substantially aligned with the shaft 42". The distal end 40d'" of the end effector 40'" illustrated in FIG. 2C is referred to a curved dissector. While the distal end 40d'" is shaped in a similar fashion with respect to the shaft 42'" as the hook configuration of the distal end 40d', the distal end 40d'" includes a blunt tip formed at its distal-most end to assist in dissecting.

A person skilled in the art will recognize that the examples of distal ends 40d, 40d', 40d", 40d'" provided for herein are not limiting, and in fact a number of other distal end or tip configurations can be used in conjunction with the disclosures provided for herein. Further, like the outer sheath 50, the end effector 40, or just the distal ends 40d, 40d', 40d", 40d'", can be removable and replaceable components of the device 10. Thus, in some embodiments, the end effector 40 can be removably and replaceably coupled to the handle portion 20 to allow for differently configured end effectors to be used with the device. Alternatively, the end effector 40 can remain coupled to the end handle portion 20 while just its distal end is removably and replaceably exchanged to achieve particular results in cutting or coagulating. A person skilled in the art will recognize particular distal end configurations that are useful for particular types of procedures or particular anatomies.

The end effector 40 can have any number of shapes, sizes, and configurations, depending, at least in part, on the sizes, shapes, and configurations of the other components of the device 10, the anatomy of the patient, and the type of procedure being performed. A length of the end effector 40 is selected so that it is long enough to reach a surgical site and is complementary to the length of the outer sheath 50 so that the outer sheath can selectively expose and cover the distal end 40d of the end effector. In some exemplary embodiments, a length of the end effector 40 is approximately in the range of about 20 centimeters to about 50 centimeters, and in one embodiment the length is about 35 centimeters. Materials typically used to form monopolar and bipolar end effectors can be used form end effectors provided for herein, and thus the end effector 40 can include, but is not limited to, stainless steel, cobalt-chromium based alloys, titanium, aluminum, and nickel alloys.

As shown, the nozzle 30 is generally cylindrical in nature and includes a housing 32 having an opening or bore 34 extending therethrough. A central longitudinal axis of the nozzle is shared with the central longitudinal axis L of the outer sheath 50. The nozzle 30 can include a mating feature that is complementary to a mating feature of the proximal end 50p of the outer sheath 50. In the illustrated embodiment, the mating feature of the nozzle includes a distal portion 34d of the bore 34 being sized to receive and hold the proximal end 50p of the outer sheath 50 by way of an interference fit. The distal portion 34d of the bore 34 can be configured to allow the outer sheath 50 to be removed from the nozzle 30 so that a different outer sheath can subsequently be coupled to the nozzle. A person skilled in the art will recognize many other configurations and locations of one or more mating features that can be used to allow the nozzle 30 to receive the outer sheath 50 in a removable and replaceable manner. In other embodiments, the outer sheath 50 may not be removable from the nozzle 30.

Figure 3A:
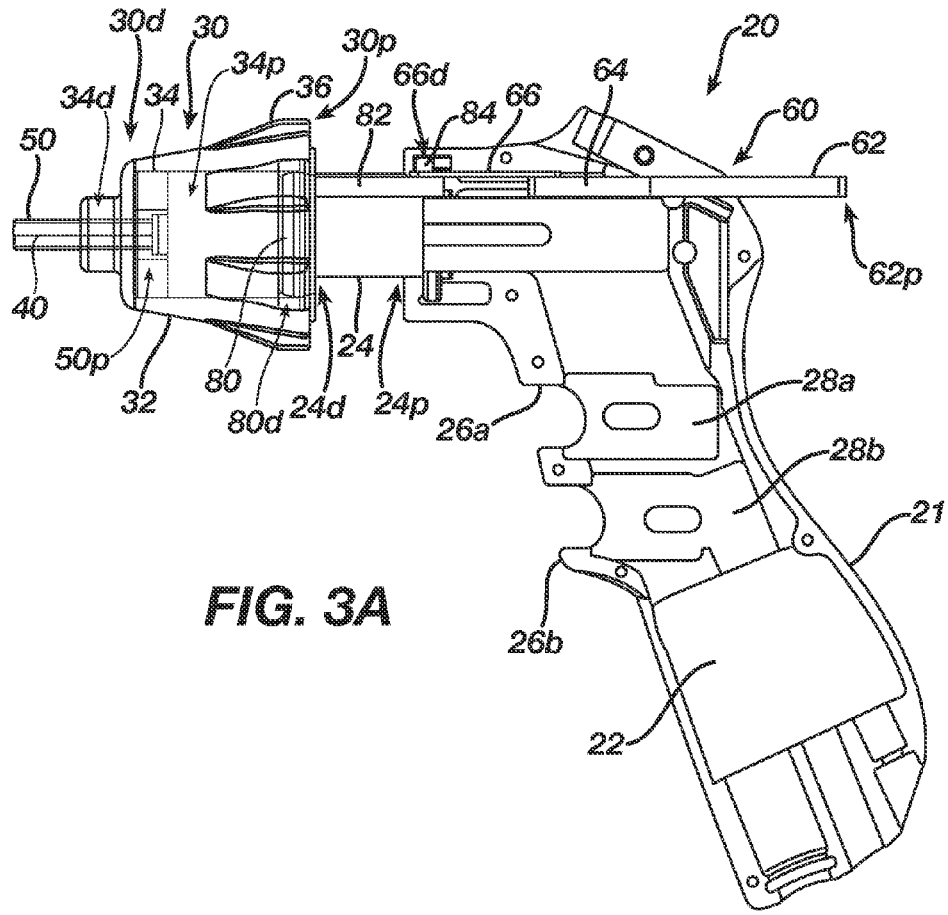
FIG. 3A is a semi-transparent side view of a handle portion and a nozzle of the surgical device of FIG. 1A.
Figure 3B:
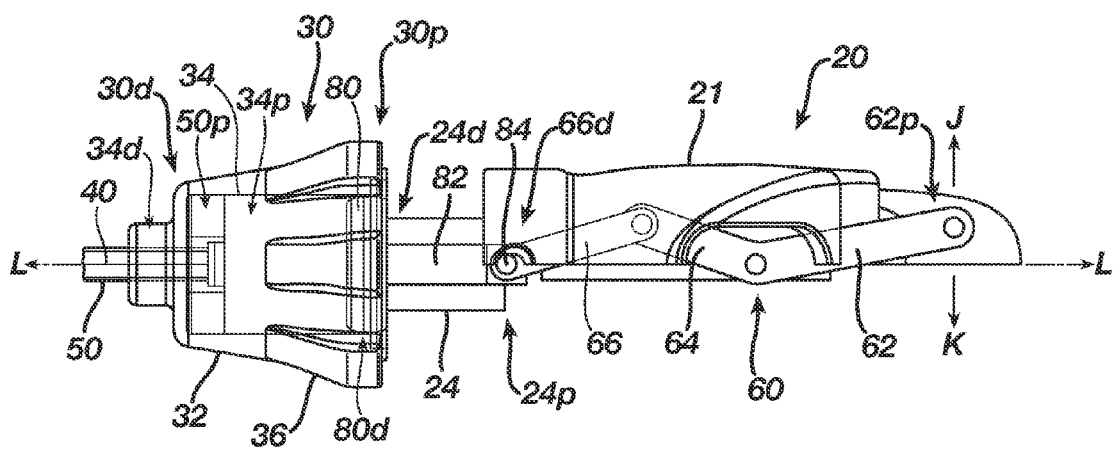
FIG. 3B is a semi-transparent, partial cross-sectional top view of the handle portion and nozzle of FIG. 3A.

A proximal portion 34p of the bore 34 can be sized to receive a distal rod 24 of the handle portion 20. As shown, the distal rod 24 can fit within the proximal portion 34p, thus allowing the nozzle 30 to translate along the distal rod 24, and thus along the longitudinal axis L. When the nozzle 30 is extended away from the handle portion 20 and is disposed on a distal end 24d of the distal rod 24, the nozzle is in an extended position, as illustrated in FIGS. 3A and 3B, and when the nozzle 30 is retracted towards the handle portion 20 and is disposed on a proximal end 24p of the distal rod 24, the nozzle is in a retracted position. The extended and retracted positions of the nozzle 30 are complementary to the extended and retracted positions of the outer sheath 50 due to the two components being coupled together. In the illustrated embodiment, the proximal portion 34p has a larger diameter than the distal portion 34d of the bore 34, although other configurations are possible, depending, at least in part, on the size, shape, and configuration of the other components of the device, e.g., the proximal end 50p of the outer sheath 50 and the distal rod 24 of the handle portion 20. The nozzle 30 can also be configured to freely rotate about the longitudinal axis L in both the clockwise and counterclockwise directions. Just as the translational movement of the nozzle 30 along the longitudinal axis L causes the outer sheath 50 to translate in the same manner because of their coupled arrangement, so too does the rotational movement of the nozzle 30 cause the outer sheath 50 to rotate in the same manner.

Like the other components of the device, the nozzle 30 can have any number of shapes, sizes, and configurations, depending, at least in part, on the sizes, shapes, and configurations of the other components of the device 10, the anatomy of the patient, and the type of procedure being performed. As shown, the cylindrically-shaped housing 32 has a diameter that is larger at a proximal end 30p than at a distal end 30d. One or more wings 36 can be formed on a portion of the housing 32. As shown, a plurality of wings 36 is disposed radially and equidistantly around a circumference of the proximal end 30p. The wings 36 can provide surfaces for a surgeon's fingers to push or pull to rotate the nozzle 30. In other embodiments, rotation of the nozzle 30 can be actuated by a control provided on the handle portion 20, such as a button configured to mechanically or electrically actuate rotation of the nozzle 30.

As shown, the handle portion 20 is generally in the shape of a pistol grip. A person having skill in the art will understand that the illustrated pistol grip is one of many configurations of a pistol grip, and the illustrated grip is in no way intended to limit the size, shape, or configuration of a pistol grip that can be used in conjunction with the disclosures herein, including the disclosures related to translating means. In fact, for illustrative and comparative purposes, the same pistol grip configuration is illustrated in conjunction with each of the embodiments illustrating both a translating means and a handle portion provided herein, even for instances in which the illustrated translating means is not suitably configured to fit with the illustrated handle portion 20. The handle portion 20 can be easily adapted and modified to better accommodate the configurations of each of the translating means disclosed herein without departing from the spirit of the present disclosure. Likewise, a person having skill in the art would be able to modify shapes, dimensions, and general configurations of the translating means provided for herein to accommodate them for variously sized, shaped, and configured handle portions without departing from the spirit of the present disclosure.

The handle portion 20 generally includes a housing 21 having a gripping section 22 around which a surgeon's hand is configured to wrap around to hold and operate the device 10, and a distal rod 24 along which the nozzle 30 is configured to translate. In some embodiments, the distal rod 24 can include a catch portion on a distal end thereof (not shown) to prevent the nozzle 30 from sliding off of the distal rod 24 as the nozzle translates distally along the rod. In other embodiments, the translating means is configured so that when the translating means is in an extended position, the nozzle 30 remains on the rod 24 and is unable to translate further distally due to the configuration of the translating means. Further, the handle portion 20 can include any number of components to operate various features of the device, including components to apply energy to the end effector 40 and components to irrigate and/or suction through the outer sheath 50. Many such components are removed from the handle portion 20 provided herein for illustrative purposes, thereby allowing the various translating means to be more easily viewed and appreciated. To the extent such components and features are not fully illustrated or described herein, a person having skill in the art will appreciate how such components and features would operate in the context of the various devices described herein.

In the illustrated embodiment, the handle portion 20 includes two finger grooves 26a, 26b formed in a distal wall 22d of the gripping section 22. As shown, each groove 26a, 26b has a button 28a, 28b associated therewith, respectively. One of the buttons 28a, 28b can be adapted to close a circuit to delivery energy to the end effector 40 as is known to those skilled in the art. The other button 28a, 28b can be adapted to initiate an irrigation function or suction function, depending on the configuration of the device, such that pushing the button passes fluid through the outer sheath 50 to irrigate the surgical site or applies a vacuum force through the outer sheath 50 to suction the site. In some embodiments, the device can perform both functions, and a toggle switch or other mechanism configured to allow for dual functionality can be provided as part of the handle portion 20 to allow a user to change whether fluid is delivered or a vacuum force is applied.

Similar to the outer sheath 50 and the end effector 40, the handle portion 20 can be a removable and replaceable component of the device 10. Different handle portions can be adapted to perform different functions or provide different parameters for similar functions. Thus, in some embodiments, one handle can be configured to provide irrigation to a surgical site, while a second handle can be configured to provide suction to a surgical site. A device provided as part of a kit can include handle portions having different sizes, shapes, configurations, and functionalities, including some of which may not be pistol grip handle portions. For example, in some embodiments, the handle portion can be what those having skill in the art refer to as a pencil grip, which provides for a grip that is substantially in-line with the longitudinal axis L, as opposed to at an angle with respect to the longitudinal axis L, as is the case for the pistol grip. While the handle portion 20 can have many different sizes, shapes, and configurations, it can generally be sized to accommodate the other components of the device 10, including the translating means. Materials used to form components of the handle portion 20 and the nozzle 30 can include but are not limited to various plastics such as polyoxymethylene copolymer (POM), polyamides, polycarbonate, polyetherimide, polyetheretherketone, polyethylene, polylactic acid/polylactide acid (PLA), polypropylene, polystyrene, polyurethane, polyvinyl chloride (PVC), and thermoplastic elastomer. In one exemplary embodiment, the outer sheath is made from polyethylene.

Translating Linkage Switch

The translating means illustrated in FIGS. 1A, 1B, 3A, and 3B is a translating linkage switch 60. As shown, the switch 60 has a plurality of linkage members 62, 64, 66, with a distal-most linkage member 66 being coupled to a carrier 80. The carrier 80 is coupled to the nozzle 30 such that distal advancement and proximal retraction of the carrier 80 by way of the switch 60 is passed on to the nozzle 30, and thus the outer sheath 50.

The translating linkage switch 60 does not necessarily include any particular number of linkages. In the illustrated embodiment, three linkage members 62, 64, 66 are provided. The proximal-most linkage member 62 is configured such that its proximal end 62p extends out of a back or proximal end 20p of the handle portion 20. This configuration allows a user to manipulate the switch 60, for instance using a finger or thumb to control the proximal-most linkage member 62, while not adjusting a grip around the gripping section 22 of the handle portion 20. A distal end 66*d* of the distal-most linkage member 66 is coupled to the carrier 80, and the middle linkage member 64 extends between the proximal-most and distal-most linkage members 62, 66. The connections between the proximal-most and middle linkage members 62, 64, the middle and distal-most linkage members 64, 66, and the distal-most linkage member 66 and the carrier 80 are pivotal connections, as is typical in a linkage configuration.

As shown, the proximal-most linkage member 62 is longer (as measured in the direction of the longitudinal axis L) than the other two linkage members 64, 66, although any of the linkage members can be longer or shorter than another, and in some embodiments, they can all have a similar length. Further, as shown in FIG. 3A in particular, the distal-most linkage member 66 is thinner than the other two linkage member 62, 64, and is mounted to a top surface of the middle linkage member 64 and a top surface of the carrier 80. Any of the linkage members, however, can be thinner or thicker than another, and in some embodiments, they can all have similar thicknesses. In further embodiments of switches provided for herein, a person having skill in the art will understand that the size, shape, and configuration of the various components of the switches can depend, at least in part, on the size, shape, and configuration of the other components of the device, and in particular the size, shape, and configuration of the carrier and the handle portion. The illustrated sizes, shapes, and configurations provided for each of the translating means described herein is not intended to be limiting.

The carrier 80 can generally be configured to link the switch 60 with the nozzle 30. As shown, the carrier 80 has a ring-shaped distal end 80*d* that is configured to sit within the proximal portion 34*p* of the bore 34 of the nozzle 30, and is coupled to an inner wall of the nozzle 30 that defines the proximal portion 34*p* of the bore 34. A diameter of the carrier 80 is generally complementary to a diameter of the distal rod 24 so that the carrier 80 can slide along a surface of the distal rod 24. The carrier 80 also includes a proximally extending arm 82 that extends from the ring-shaped distal end 80*d* and towards the proximal end 20*p* of the handle portion 20. The arm 82 can be substantially parallel to the longitudinal axis L to aid in promoting smooth translation of the carrier 80, nozzle 30, and outer sheath 50. The arm 82 can include a tab or pin 84 formed on its proximal end 82*p* to receive a bore formed on the distal end 66*d* of the distal-most linkage member 66 to form the pivotal connection therebetween. In the illustrated embodiment, the arm 82 extends from a top end of the ring-shaped distal end 80*d*, although the arm 82 can extend from any location along the ring-shaped distal end 80*d*. A size and shape of the arm 82, and of the carrier 80 more generally, can be based, at least in part, on the configurations of the other components with which it is used, and in particular a size, shape, and configuration of the nozzle 30 and the translating means 60. In further embodiments of a carrier provided for herein, a person having skill in the art will understand that the size, shape, and configuration of the carrier can depend, at least in part, on the size, shape, and configuration of the other components of the device, and in particular the size, shape, and configuration of the translating means and the nozzle.

In use, a surgeon can push the proximal-most linkage member 62 in a first direction J that is substantially perpendicular to the longitudinal axis L (as shown in FIG. 3B) to slide the nozzle 30 distally along the distal rod 24, towards the distal end of the end effector, until the nozzle 30 reaches the extended position, as shown in each of FIGS. 1A, 1B, 3A, and 3B. The advancing movement of the nozzle 30 causes the distal end 50*d* of the outer sheath 50 to also advance distally to its extended position, as shown in FIGS. 1A and 1B, in which the distal end 50*d* extends over or covers the distal end 40*d* of the end effector 40. The surgeon can push the proximal-most linkage member 62 with a finger or thumb of the same hand holding the gripping section 22 of the handle portion 20 without adjusting his or her grip on the gripping section 22.

Likewise, a surgeon can push the proximal-most linkage member 62 in a second, opposite direction K (as shown in FIG. 3B) to slide the nozzle 30 proximally along the distal rod 24, towards the proximal end 20*p* of the handle portion 20, until the nozzle reaches the retracted position (not shown). The retracting movement of the nozzle 30 causes the distal end 50*d* of the outer sheath 50 to also retract proximally to its retracted position (not shown) in which the distal end 50*d* is proximal to the distal end 40*d* of the end effector 40, thereby exposing the distal end 40*d*. Again the surgeon can pull the proximal-most linkage member 62 with a finger or thumb of the same hand holding the gripping section 22 of the handle portion 20 without adjusting his or her grip on the gripping section 22.

Rocker Switch

Figure 4:
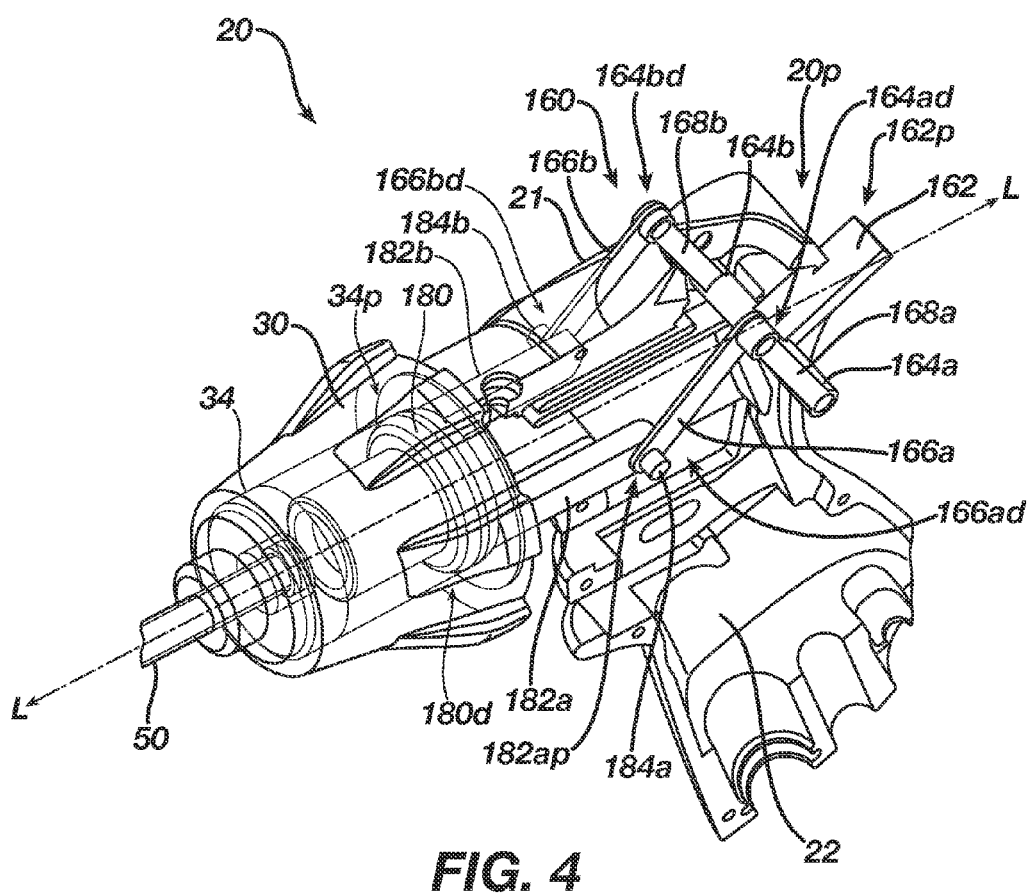
FIG. 4 is a semi-transparent perspective view of one exemplary embodiment of a handle portion and a nozzle of a surgical device.
Figure 5A:
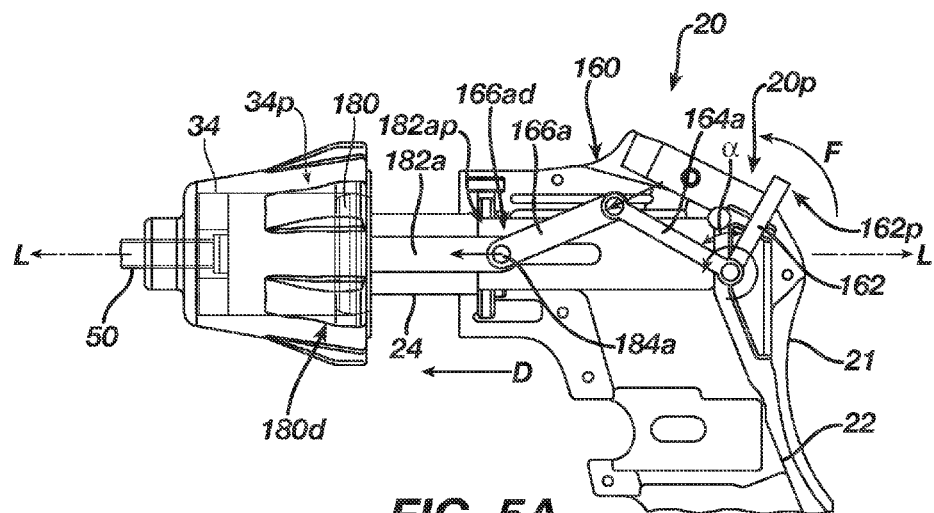
FIG. 5A is a semi-transparent side view of the handle portion and nozzle of FIG. 4 in which the nozzle is disposed in an extended position.
Figure 5B:
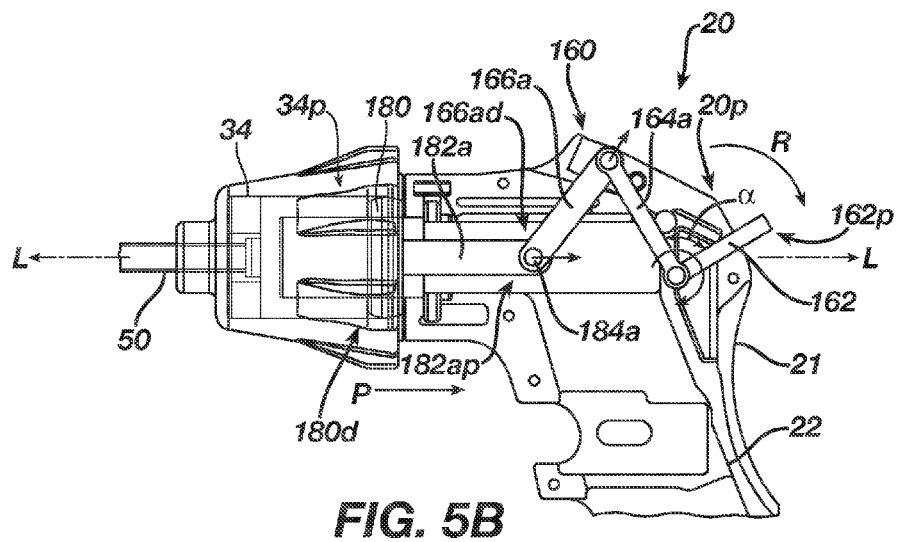
FIG. 5B is a semi-transparent side view of the handle portion and nozzle of FIG. 4 in which the nozzle is disposed in a retracted position.

The translating means illustrated in FIGS. 4, 5A, and 5B is a rocker switch 160. As shown, the switch 160 has a plurality of bars or segments 162, 164*a*, 164*b*, 166*a*, 166*b*, with the distal-most bars or segments 166*a*, 166*b* being coupled to a carrier 180. The carrier 180 is coupled to the nozzle 30 such that distal advancement and proximal retraction of the carrier 180 by way of the switch 160 is passed on to the nozzle 30, and thus the outer sheath 50.

The rocker switch 160 does not necessarily include any particular number of segments. In the illustrated embodiment, five bars or segments 162, 164*a*, 164*b*, 166*a*, 166*b* are provided, with the proximal-most segment 162 being coupled to each of the two middle segments 164*a*, 164*b* by a frame bar 168*a* extending substantially perpendicular to the proximal-most segment 162, and a second frame bar 168*b* extending between distal ends 164*ad*, 164*bd* of the segments 164*a*, 164*b* to provide stability. The proximal-most segment 162 is configured such that its proximal end 162*p* extends out of a proximal end 20*p* of the handle portion 20. In the illustrated embodiment, the proximal end 162*p* is exposed out of a portion of the housing 21 that transitions from the back end to the top portion, although other positions that are accessible to the same hand of the user that is holding the gripping section 22 without the user having to change his or her grip on the gripping section are possible. Distal end 166*ad*, 166*bd* of the distal-most segments 166*a*, 166*b* are coupled to the carrier 80, and the middle segments 164*a*, 164*b* extend between the proximal-most segment 162 and the distal-most segments 166*a*, 166*b*. The connections between the middle and distal-most segments 164*a*, 164*b*, 166*a*, 166*b* and the distal-most segments 166*a*, 166*b* and the carrier 180 are pivotal connections, while the connection between the proximal-most segment 162 and the middle segments 164*a*, 164*b* is substantially fixed, and in fact, the proximal-most segment 162, the middle segments 164*a*, 164*b*, and the frame bar 168*a* extending therebetween can form a single component or segment. As a result, when the proximal-most segment 162 is subjected to a force in a counterclockwise direction F, as shown in FIG. 5A, or to a force in a clockwise direction R, as shown in FIG. 5B, an angle α formed between the proximal-most and middle segments 162, 164a, 164b stays substantially the same, while the middle and distal-most segments 164a, 164b, 166a, 166b pivot at the other respective pivotal connections to move the nozzle 30 to the extended position (FIG. 5A) and the retracted position (FIG. 5B).

As shown, the proximal-most segment 162 is shorter (as measured in the direction of the longitudinal axis L) than the other segments 164a, 164b, 166a, 166b. Further, as shown in FIG. 5 in particular, the proximal-most segment 162 is thicker than the middle segments 164a, 164b, which themselves are thicker than the distal-most segments 166a, 166b. The thicker proximal-most segment 162 allows easy engagement by a user's fingers or thumb while still maintaining his or her original grip on the gripping section 22.

The carrier 180 can generally be configured to link the switch 160 with the nozzle 30. As shown, the carrier 180 has a ring-shaped distal end 180d that is configured to sit within the proximal portion 34p of the bore 34 of the nozzle 30, and is coupled to an inner wall of the nozzle that defines the proximal portion 34p of the bore 34. A diameter of the carrier 180 is generally complementary to a diameter of the distal rod 24 so that the carrier 180 can slide along a surface of the distal rod 24. The carrier 180 also includes two proximally-extending, opposed arms 182a, 182b that extend from the ring-shaped distal end 180d and towards the proximal end 20p of the handle portion 20. The arms can be substantially parallel to and disposed on opposite sides of the longitudinal axis L to aid in promoting smooth translation of the carrier 180, nozzle 30, and outer sheath 50. The arms 182a, 182b can include a tab or pin 184a, 184b formed on their respective proximal ends 182ap, 182bp to receive a bore formed on the respective distal ends 166ad, 166bd of the distal-most segments 166a, 166b, forming the pivotal connections therebetween. In the illustrated embodiment, the arms 182a, 182b extend from a central section of the ring-shaped distal end 180d.

In use, a surgeon can push the proximal-most segment 162 in the counterclockwise direction F to slide the nozzle 30 distally along the distal rod 24 in a direction D, towards the distal end of the end effector, until the nozzle 30 reaches the extended position, as shown in FIG. 5A. The advancing movement of the nozzle 30 causes the distal end of the outer sheath to also advance distally to its extended position and cover the distal end of the end effector. The surgeon can push the proximal-most segment 162 with a finger or thumb of the same hand holding the gripping section 22 of the handle portion 20 without adjusting his or her grip on the gripping section 22.

Likewise, a surgeon can pull the proximal-most segment 162 in a clockwise direction R to slide the nozzle proximally along the distal rod 24 in a direction P, towards the back end 20p of the handle portion 20, until the nozzle reaches the retracted position, as shown in FIG. 5B. The retracting movement of the nozzle 30 causes the distal end of the outer sheath to also retract proximally to its retracted position and expose the distal end of the end effector. The surgeon can pull the proximal-most segment 162 with a finger or thumb of the same hand holding the gripping section 22 of the handle portion 20 without adjusting his or her grip on the gripping section 22.

Pivot Switch

Figure 6:
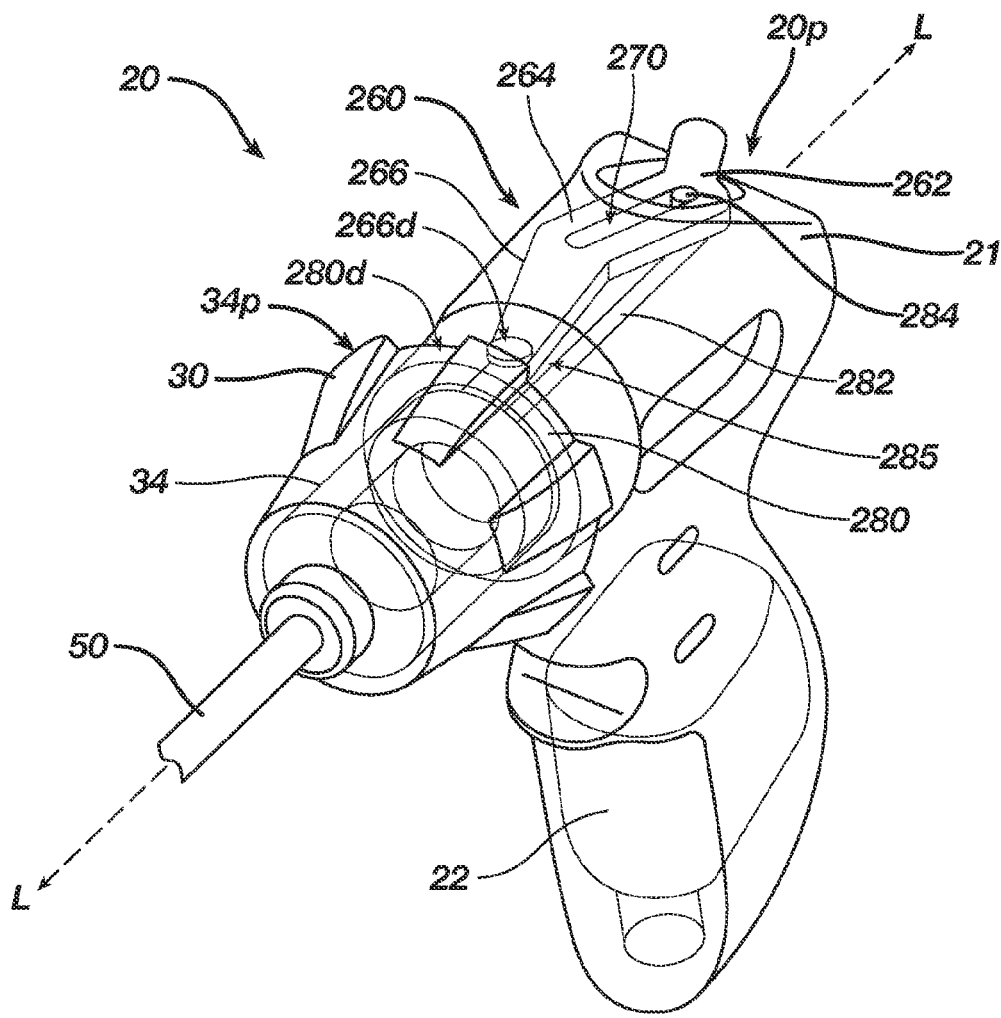
FIG. 6 is a semi-transparent perspective view of another exemplary embodiment of a handle portion and a nozzle of a surgical device.
Figure 7A:
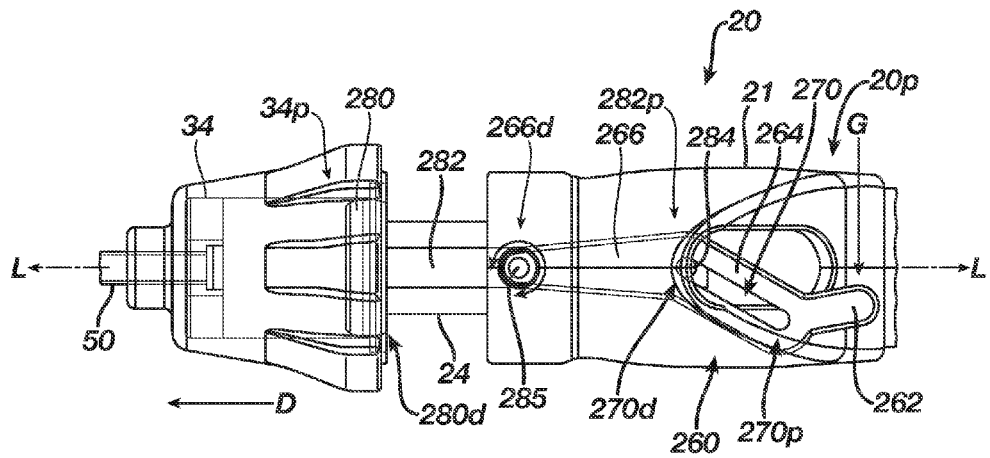
FIG. 7A is a semi-transparent top view of the handle portion and nozzle of FIG. 6 in which the nozzle is disposed in an extended position.
Figure 7B:
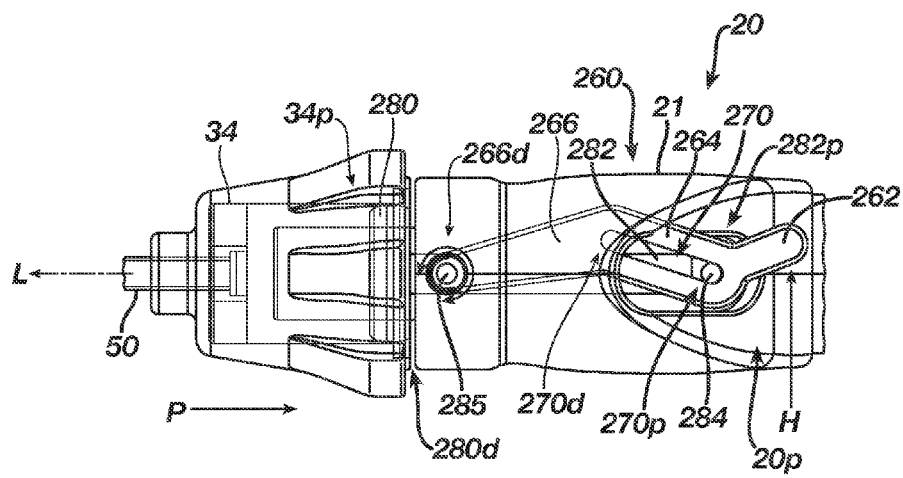
FIG. 7B is a semi-transparent top view of the handle portion and nozzle of FIG. 6 in which the nozzle is disposed in a retracted position.

The translating means illustrated in FIGS. 6, 7A, and 7B is a pivot switch 260. As shown, the switch 260 includes a single arm having a proximal segment 262, an intermediate segment 264, and a distal segment 266, with the distal segment 266 being coupled to the housing 21. The carrier 280 is coupled to the nozzle 30 such that distal advancement and proximal retraction of the carrier 280 by way of the switch 260 is passed on to the nozzle 30, and thus the outer sheath 50.

As shown, the proximal segment 262 of the switch 260 extends out of a proximal end 20p of the handle portion 20, and more particularly out of a portion of the housing 21 that transitions from the back end to the top portion to allow it to be accessible to the same hand of the user that is holding the gripping section 22 without the user having to change his or her grip on the gripping section. The intermediate segment 264 includes an elongate channel 270 formed therein for receiving a pin or tab 284 of the carrier 280. The tab 284 can be configured to translate along a length of the channel 270 during distal advancement and proximal retraction. A distal end 266d of the distal segment 266 is pivotally coupled to the housing 21 at pivot point 285. In the illustrated embodiment, the proximal and intermediate segments 262, 264 extend at an angle with respect to the longitudinal axis L in both the extended position (FIG. 7A) and the retracted position (FIG. 7B), while the distal segment 266 is parallel to and substantially aligned with the longitudinal axis L in the extended position, and disposed at an angle with respect to the longitudinal axis L in the retracted position. Further, a length (as measured in the direction of the longitudinal axis L) of the proximal segment 262 is substantially smaller than the lengths of the intermediate and distal segments 264, 266, which have substantially similar lengths. The length of the channel 270 is approximately equal to the length traveled by the nozzle 30 and the outer sheath 50 when they move from their respective retracted positions to their respective extended positions.

The carrier 280 can generally be configured to link the switch 260 with the nozzle 30. As shown, the carrier 280 has a ring-shaped distal end 280d that is configured to sit within the proximal portion 34p of the bore 34 of the nozzle 30, and is coupled to an inner wall of the nozzle that defines the proximal portion 34p of the bore 34. A diameter of the carrier 280 is generally complementary to a diameter of the distal rod 24 so that the carrier 280 can slide along a surface of the distal rod 24. The carrier 280 also includes a proximally extending arm 282 that extends from a top portion of the ring-shaped distal end 280d and towards the proximal end 20p of the handle portion 20. The arm 282 can be substantially parallel to the longitudinal axis L, and can include a pin or tab 284 formed thereon that sits within the channel 270. As shown, the tab 284 is disposed at a distal end 270d of the channel 270 when the nozzle is in the extended position (FIG. 7A), and at a proximal end 270p of the channel 270 when the nozzle is in the retracted position (FIG. 7B). The nozzle and the outer sheath can only travel as far distally and proximally as the combination of the tab 284 and the channel 270 will allow them to travel. As the tab 284 moves through the channel, the switch 260 pivots with respect to the housing 21 at the pivot point 285.

In use, a surgeon can push the proximal section 262 in a first direction G, which as shown is a direction that is substantially perpendicular to the longitudinal axis L, to slide the nozzle 30 distally along the distal rod 24 in a direction D, towards the distal end of the end effector, until the nozzle 30 reaches the extended position, as shown in FIG. 7A. As illustrated by comparing FIG. 7A to FIG. 7B, the orientation of the three segments 262, 264, and 266 with respect to the longitudinal axis L changes as the tab 284 slides towards the distal end 270d of the channel 270 in response to the force in the direction G. Further, the advancing movement of the nozzle 30 causes the distal end of the outer sheath to also advance distally to its extended position and cover the distal end of the end effector. The surgeon can push the proximal segment 262 with a finger or thumb of the same hand holding the gripping section 22 of the handle portion 20 without adjusting his or her grip on the gripping section 22.

Likewise a surgeon can push the proximal segment 262 in a second direction H, which is opposed to the direction G and is thus also substantially perpendicular to the longitudinal axis L, to slide the nozzle 30 proximally along the distal rod 24 in a direction P to reach the retracted position, as shown in FIG. 7B. As illustrated by comparing FIG. 7A to FIG. 7B, the orientation of the three segments 262, 264, and 266 with respect to the longitudinal axis L changes as the tab 284 slides towards the proximal end 270p of the channel 270 in response to the force in the direction H. Further, the retracting movement of the nozzle 30 causes the distal end of the outer sheath to also retract proximally to its retracted position and exposes the distal end of the end effector. The surgeon can push the proximal segment 262 with a finger or thumb of the same hand holding the gripping section 22 of the handle portion 20 without adjusting his or her grip on the gripping section 22.

Toggle Switch

Figure 8:
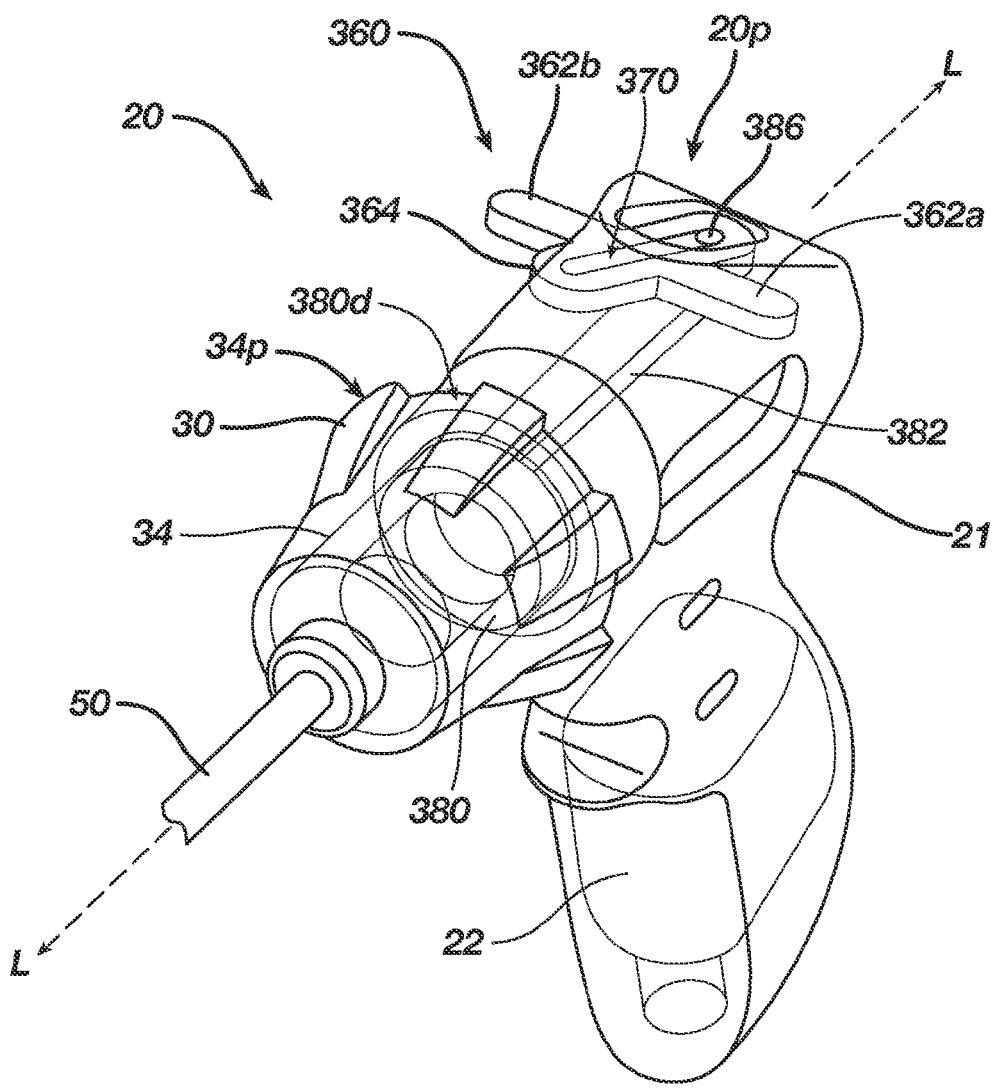
FIG. 8 is a semi-transparent perspective view of yet another exemplary embodiment of a handle portion and a nozzle of a surgical device.
Figure 9A:
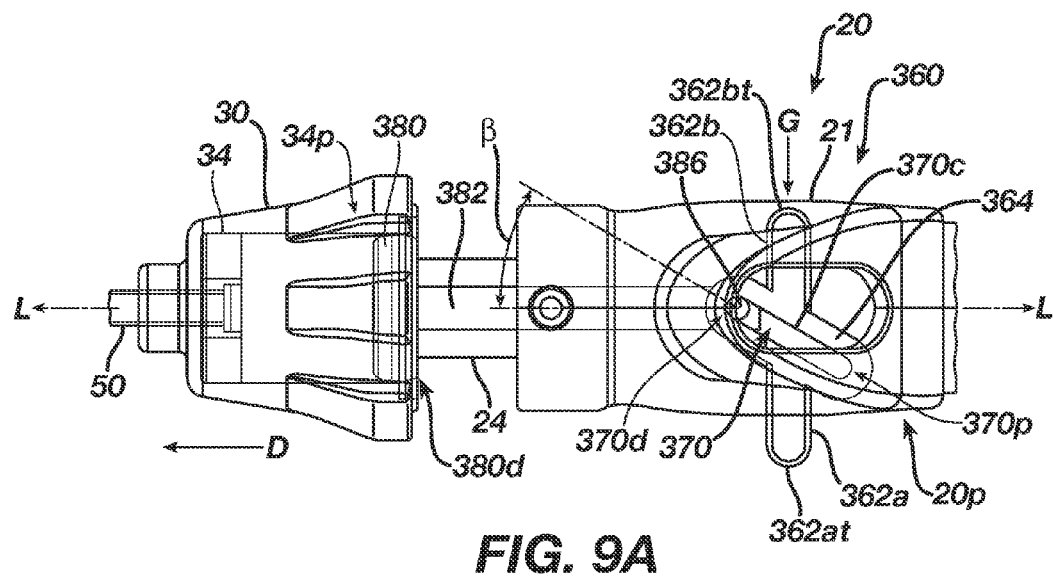
FIG. 9A is a semi-transparent top view of the handle portion and nozzle of FIG. 8 in which the nozzle is disposed in an extended position.
Figure 9B:
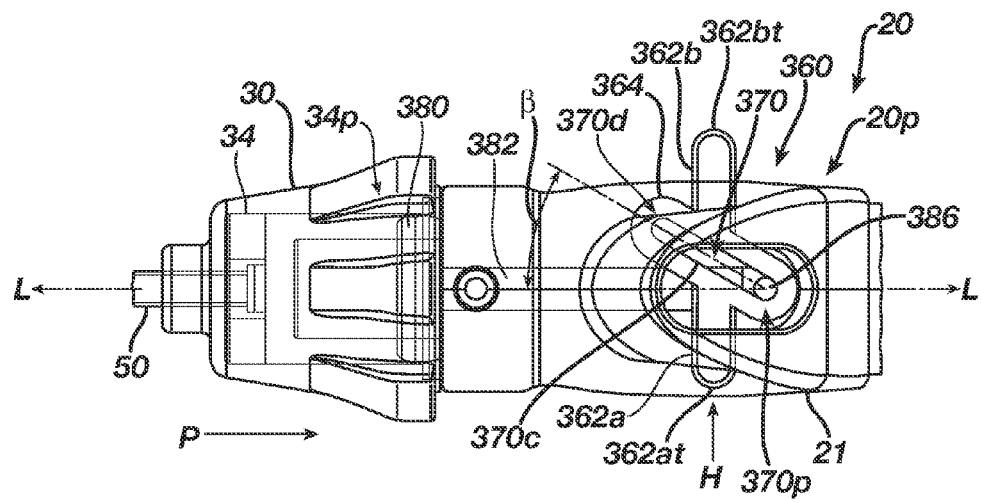
FIG. 9B is a semi-transparent top view of the handle portion and nozzle of FIG. 8 in which the nozzle is disposed in a retracted position.

The translating means illustrated in FIGS. 8, 9A, and 9B is a toggle switch 360. As shown, the switch 360 includes a body 364 having a centrally disposed channel 370 formed therein and first and second actuation arms 362a, 362b extending from opposed sides of the channel 370. The switch 360 is coupled to a carrier 380, and the carrier 380 is coupled to the nozzle 30 such that distal advancement and proximal retraction of the carrier 380 by way of the switch 360 is passed on to the nozzle 30, and thus the outer sheath 50.

As shown, the body 364 of the switch 360 has a centrally disposed channel 370 formed therein. The channel forms an angle β with the longitudinal axis L, and receives a pin or tab 386 of the carrier 380. The tab 386 can be configured to translate along a length of the channel 370 during distal advancement and proximal retraction. The first and second actuation arms 362a, 362b extend from opposite sides of a central portion 370c of the channel, the arms 362a, 362b being substantially perpendicular to the longitudinal axis L. The arms 362a, 362b generally have a similar length, with the length being long enough so that when the nozzle is in the extended position, a terminal end 362at of the first arm 362a extends outside one side of the housing 21, and when the nozzle is in the retracted position, a terminal end 362bt of the second arm 362b extends outside an opposite side of the housing 21. A surgeon operates the switch 360 by pushing one of the arms 362a, 362b in a direction G or H, which is substantially perpendicular to the longitudinal axis L. By keeping one terminal end 362at, 362bt within the housing 21 and the other outside of the housing 21, it is easy for the surgeon to know which way to push the switch 360 to actuate the nozzle 30 and outer sheath 50. The surgeon is able to move the switch 360 in either direction G or H without moving his or her hand from a grip established on the gripping portion by the surgeon when initially holding and moving the device to the surgical site.

The carrier 380 can generally be configured to link the switch 360 with the nozzle 30. As shown, the carrier 380 has a ring-shaped distal end 380d that is configured to sit within the proximal portion 34p of the bore 34 of the nozzle 30, and is coupled to an inner wall of the nozzle that defines the proximal portion 34p of the bore 34. A diameter of the carrier 380 is generally complementary to a diameter of the distal rod 24 so that the carrier 380 can slide along a surface of the distal rod 24. The carrier 380 also includes a proximally extending arm 382 that extends from a top portion of the ring-shaped distal end 380d and towards the proximal end 20p of the handle portion 20. The arm 382 can be substantially parallel to the longitudinal axis L, and can include a pin or tab 386 formed on a proximal end 382p of the arm 382. The tab 386 sits within the channel 370. As shown, the tab 386 is disposed at a distal end 370d of the channel 370 when the nozzle is in the extended position (FIG. 9A), and at a proximal end 370p of the channel 370 when the nozzle is in the retracted position (FIG. 9B).

In use, a surgeon can push the first actuation arm 362a in a first direction G, which as shown is a direction that is substantially perpendicular to the longitudinal axis L, to slide the nozzle 30 distally along the distal rod 24 in a direction D, towards the distal end of the end effector, until the nozzle 30 reaches the extended position, as shown in FIG. 9A. The advancing movement of the nozzle 30 causes the distal end of the outer sheath to also advance distally to its extended position and cover the distal end of the end effector. The surgeon can push the first actuation arm 362a with a finger or thumb of the same hand holding the gripping section 22 of the handle portion 20 without adjusting his or her grip on the gripping section 22.

Likewise, a surgeon can push the second actuation arm 362b in a second direction H, which is opposed to the direction G and is thus also substantially perpendicular to the longitudinal axis L, to slide the nozzle 30 proximally along the distal rod 24 in a direction P to reach the retracted position, as shown in FIG. 9B. The angle β formed between the channel 370 and the longitudinal axis L does not generally change as the switch 360 moves between the extended and retracted positions. The retracting movement of the nozzle 30 does cause the distal end of the outer sheath to also retract proximally to its retracted position, and thus exposes the distal end of the end effector. The surgeon can push the second actuation arm 362b with a finger or thumb of the same handle holding the gripping section 22 of the handle portion 20 without adjusting his or her grip on the gripping section 22.

Slider Switch

Figure 10:
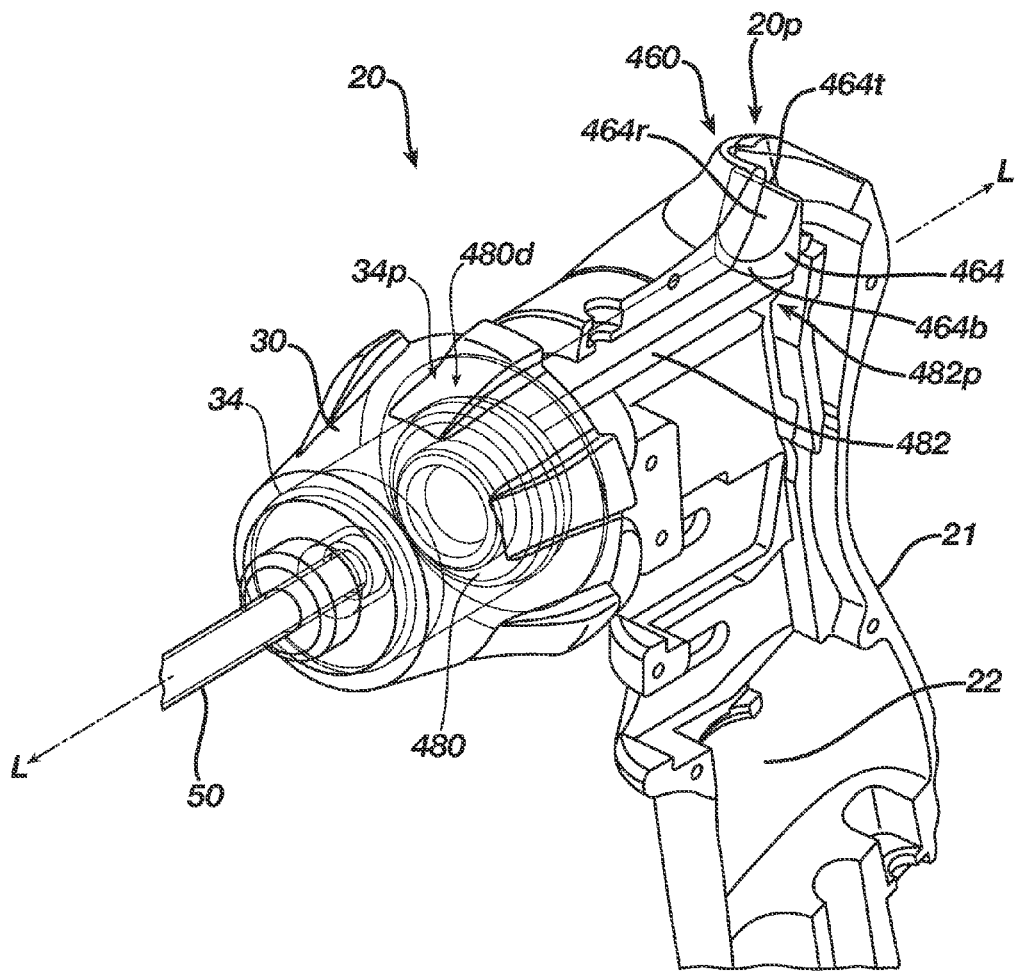
FIG. 10 is a semi-transparent perspective view of still another exemplary embodiment of a handle portion and a nozzle of a surgical device.
Figure 11A:
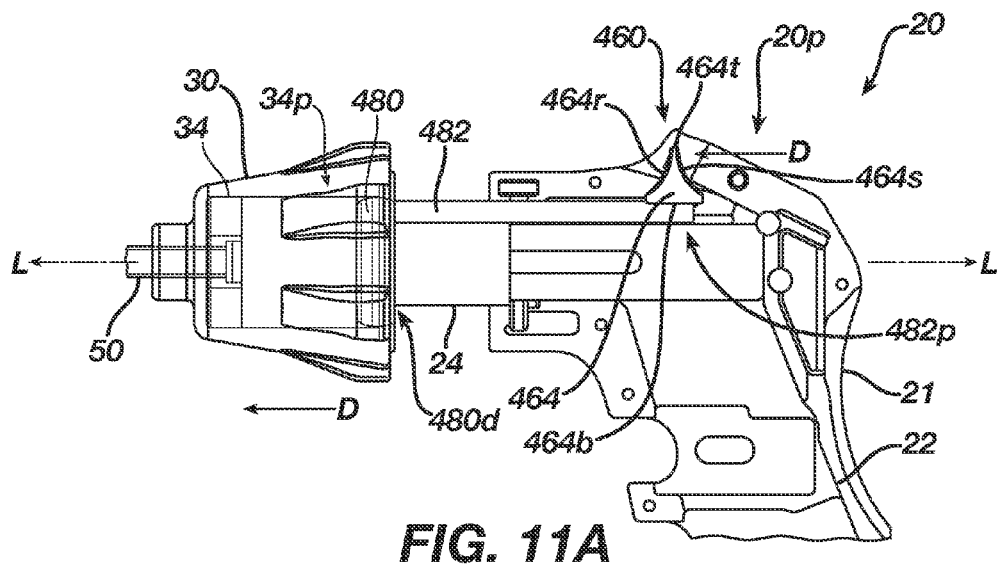
FIG. 11A is a semi-transparent side view of the handle portion and nozzle of FIG. 10 in which the nozzle is disposed in an extended position.
Figure 11B:
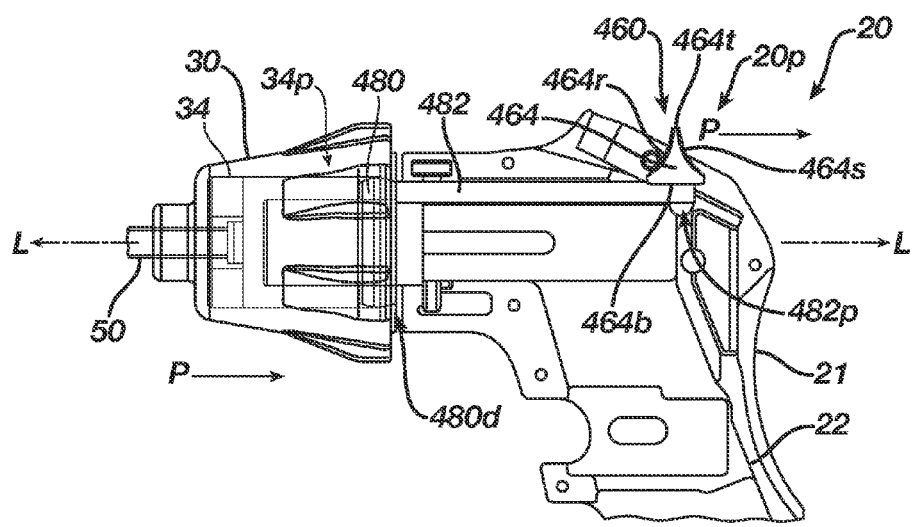
FIG. 11B is a semi-transparent side view of the handle portion and nozzle of FIG. 10 in which the nozzle is disposed in a retracted position.

The translating means illustrated in FIGS. 10, 11A, and 11B is a slider switch 460. As shown, the switch 460 includes a body 464 that is attached to a carrier 480 such that force applied to the switch 460 is directly applied to the carrier 480. The carrier 480 is coupled to the nozzle 30 such that distal advancement and proximal retraction of the carrier 480 by way of the switch 460 is passed on to the nozzle 30, and thus the outer sheath 50.

As shown, the body 464 of the switch 460 is a tab that is ergonomically formed to receive a thumb of a user. In the illustrated embodiment, the body 464 includes opposed flat surfaces 464r, 464s that have a rounded taper in an upwards direction, meeting at a top 464t. A base 464b of the body 464 can be configured to couple to a proximal end 482p of an arm 482 extending from the carrier 480. A person skilled in the art will recognize any other number of shapes and configurations of the surfaces of the body 464 that can be used to allow a user's finger or thumb to engage the switch 460 and impart a force thereto in a direction substantially parallel to the longitudinal axis L. In the illustrated embodiment, the switch 460 is configured to extend out of the housing 21 at top portion of the handle portion 20, at a proximal position that allows the switch 460 to be operated by the same hand of the user that is holding the gripping section 22 without the user having to change his or her grip on the gripping section.

The carrier 480 can generally be configured to link the switch 460 with the nozzle 30. As shown, the carrier 480 has a ring-shaped distal end 480*d* that is configured to sit within the proximal portion 34*p* of the bore 34 of the nozzle 30, and is coupled to an inner wall of the nozzle that defines the proximal portion 34*p* of the bore 34. A diameter of the carrier 480 is generally complementary to a diameter of the distal rod 24 so that the carrier 480 can slide along a surface of the distal rod 24. The carrier 480 also includes a proximally extending arm 482 that extends from a top portion of the ring-shaped distal end 480*d* and towards the proximal end 20*p* of the handle portion 20. A proximal end 482*p* of the arm 480 is configured to receive the switch 460 by any known way of coupling two features together, including but not limited to mechanical connections and adhesives.

In use, a surgeon can push against the surface 464*s* of the switch 460 in a distal direction D to slide the nozzle 30 distally along the distal rod 24, towards the distal end of the end effector, until the nozzle 30 reaches the extended position, as shown in FIG. 11A. The advancing movement of the nozzle 30 causes the distal end of outer sheath to also advance distally to its extended position and cover the distal end of the end effector. The surgeon can push against the surface 464*s* with a thumb of the same hand holding the gripping section 22 of the handle portion 20 without adjusting his or her grip on the gripping section 22.

Likewise, a surgeon can pull against the surface 464*r* of the switch 460 in a proximal direction P to slide the nozzle 30 proximally along the distal rod 24, towards the proximal end 20*p* of the handle portion 20, until the nozzle reaches the retracted position, as shown in FIG. 11B. The retracting movement of the nozzle 30 causes the distal end of the outer sheath to also retract proximally to its retracted position and exposes the distal end of the end effector. The surgeon can pull against the surface 464*r* with a thumb of the same hand holding the gripping section 22 of the handle portion 20 without adjusting his or her grip on the gripping section 22.

Thumbwheel

Figure 12:
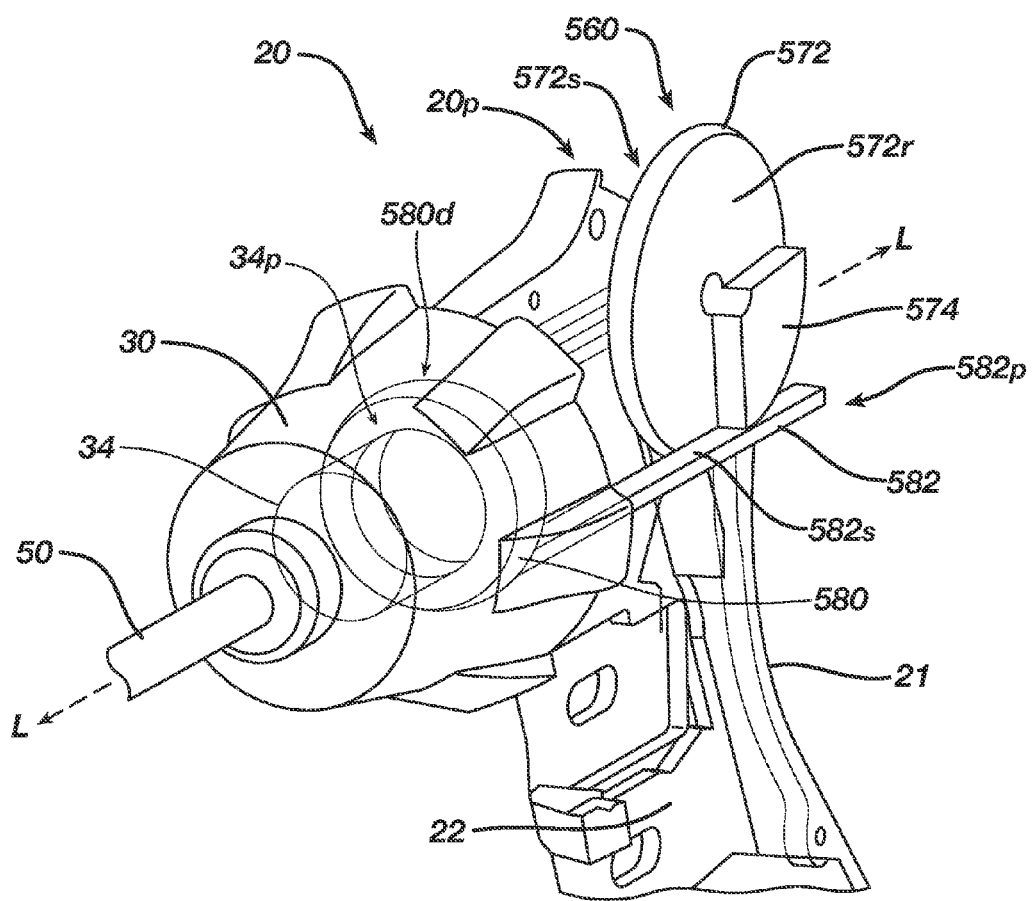
FIG. 12 is a semi-transparent perspective view of another exemplary embodiment of a handle portion and a nozzle of a surgical device.
Figure 13A:
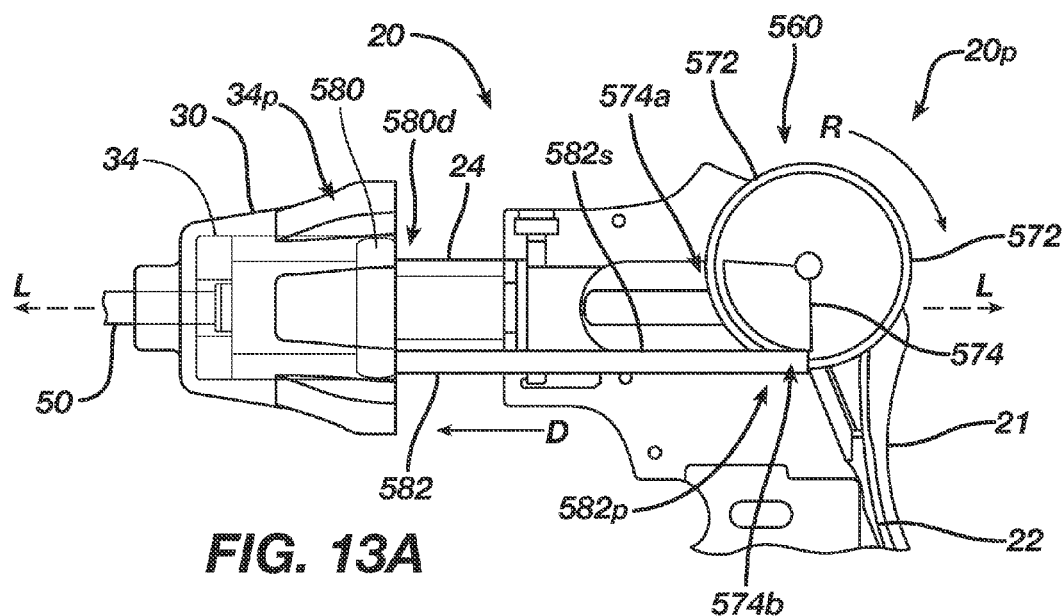
FIG. 13A is a semi-transparent side view of the handle portion and nozzle of FIG. 12 in which the nozzle is disposed in an extended position.
Figure 13B:
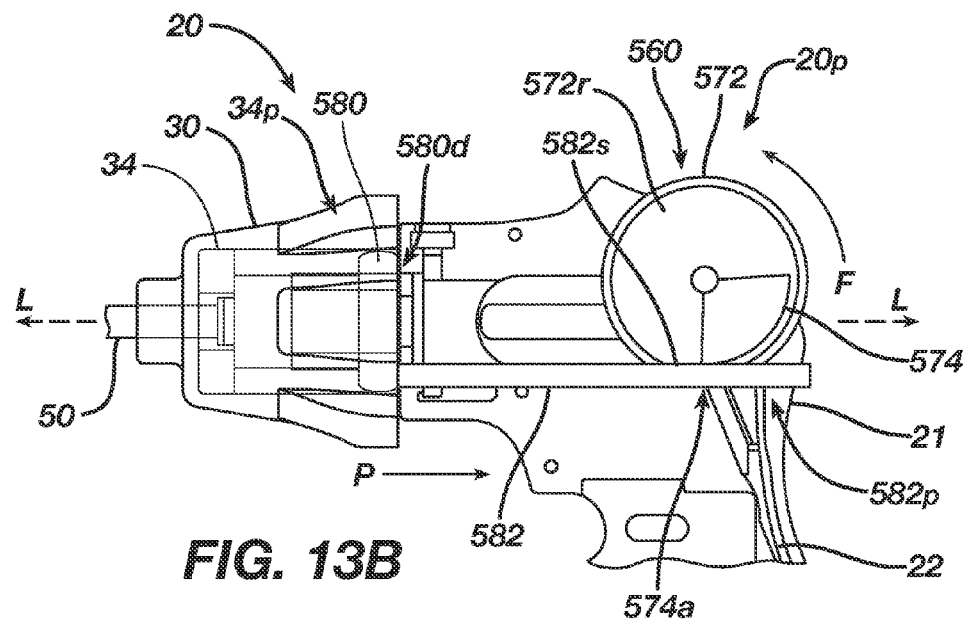
FIG. 13B is a semi-transparent side view of the handle portion and nozzle of FIG. 12 in which the nozzle is disposed in a retracted position.

The translating means illustrated in FIGS. 12, 13A, and 13B is a thumbwheel 560. As shown, the thumbwheel 560 includes a body 572 having a partial pinion gear 574 associated with one of two opposed surfaces 572*r*, 572*s* of the body 572. The thumbwheel 560 is in communication with a carrier 580, and the carrier 580 is coupled to the nozzle 30 such that distal advancement and proximal retraction of the carrier 380 by way of the thumbwheel 560 is passed on to the nozzle 30, and thus the outer sheath 50.

As shown, the body 572 of the thumbwheel 560 is substantially circular having opposed surfaces 572*r*, 572*s* that define a thickness of the body 572. A partial pinion gear 574 is formed on or otherwise associated with the surface 572*s*, and is configured to engage a portion of the carrier 580 to advance and retract the carrier 580, and thus the nozzle 30 and outer sheath 50. For example, although not illustrated, the partial pinion gear 574 can have a plurality of teeth formed on its outer surface 574*s*. In the illustrated embodiment, the partial pinion gear 574 covers approximately one-quarter of the surface area of the surface 572*s*, although other configurations in which the partial pinion gear 574 covers more or less of the surface area of the surface 572 are possible. In the illustrated embodiment, the thumbwheel 560 is configured to extend out of the housing 21 at a proximal portion 20*p* of the handle portion 20 so that the thumbwheel 560 can be rotated by the same hand of the user that is holding the gripping section 22 without the user having to change his or her grip on the gripping section.

The carrier 580 can generally be configured to link the thumbwheel 560 with the nozzle 30. As shown, the carrier 580 has a ring-shaped distal end 580*d* that is configured to sit within the proximal portion 34*p* of the bore 34 of the nozzle, and is coupled to an inner wall of the nozzle that defines the proximal portion 34*p* of the bore 34. A diameter of the carrier 580 is generally complementary to a diameter of the distal rod 24 so that the carrier 580 can slide along a surface of the distal rod 24. The carrier 580 also includes a proximally extending arm or rack 582 that extends from a bottom portion of the ring-shaped distal end 580*d* and towards the proximal end 20*p* of the handle portion 20. The arm 582 can be configured to engage with the partial pinion gear 574 to effect movement of the nozzle 30. The arm 582 can be substantially parallel to the longitudinal axis L, and can include features that are complementary to features of the partial pinion gear 574 to effect advancement and retraction of the carrier 580 in response to rotation of the thumbwheel 560. Accordingly, although not illustrated, the arm 582 can include complementary teeth formed on its top surface 582*s* so that the teeth on the arm 582 can engage with the teeth on the partial pinion gear 574 to drive the carrier 580, and thus the nozzle 30 and outer sheath 50.

In use, a surgeon can rotate the thumbwheel 560 in a clockwise direction R to drive the carrier 580 forward, i.e., distally advance the carrier 580, which in turn slides the nozzle 30 distally along the distal rod 24 in a direction D, towards the distal end of the end effector, until the nozzle 30 reaches the extended position, as shown in FIG. 13A. In the extended position, a second end 574*b* of the partial pinion gear 574 can be the portion engaged with the arm 582, and it can be engaged with a proximal end 582*p* of the arm 582. The advancing movement of the nozzle 30 causes the distal end of the outer sheath to also advance distally to its extended position and cover the distal end of the end effector. The surgeon can push the thumbwheel 560 with a finger or thumb of the same hand holding the gripping section 22 of the handle portion 20 without adjusting his or her grip on the gripping section 22.

Likewise, a surgeon can push the thumbwheel 560 in a counter clockwise direction F to drive the carrier 580 backwards, i.e., proximally retract the carrier 580, which in turn slides the nozzle 30 proximally along the distal rod 24 in a direction P, towards the proximal end 20*p* of the handle portion 20, until the nozzle reaches the retracted position, as shown in FIG. 13B. In the retracted position, a first end 574*a* of the partial pinion gear 574 can be the portion engaged with the arm 582, and it can be engaged with a portion of the arm 582 that is distal of the proximal end 582*p*. The retracting movement of the nozzle 30 causes the distal end of the outer sheath to also retract proximally to its retracted position and expose the distal end of the end effector. The surgeon can push the thumbwheel 560 with a finger or thumb of the same hand holding the gripping section 22 of the handle portion 20 without adjusting his or her grip on the gripping section 22.

Push-Pull Ring—Ring Proximal of Gripping Section

Figure 14:
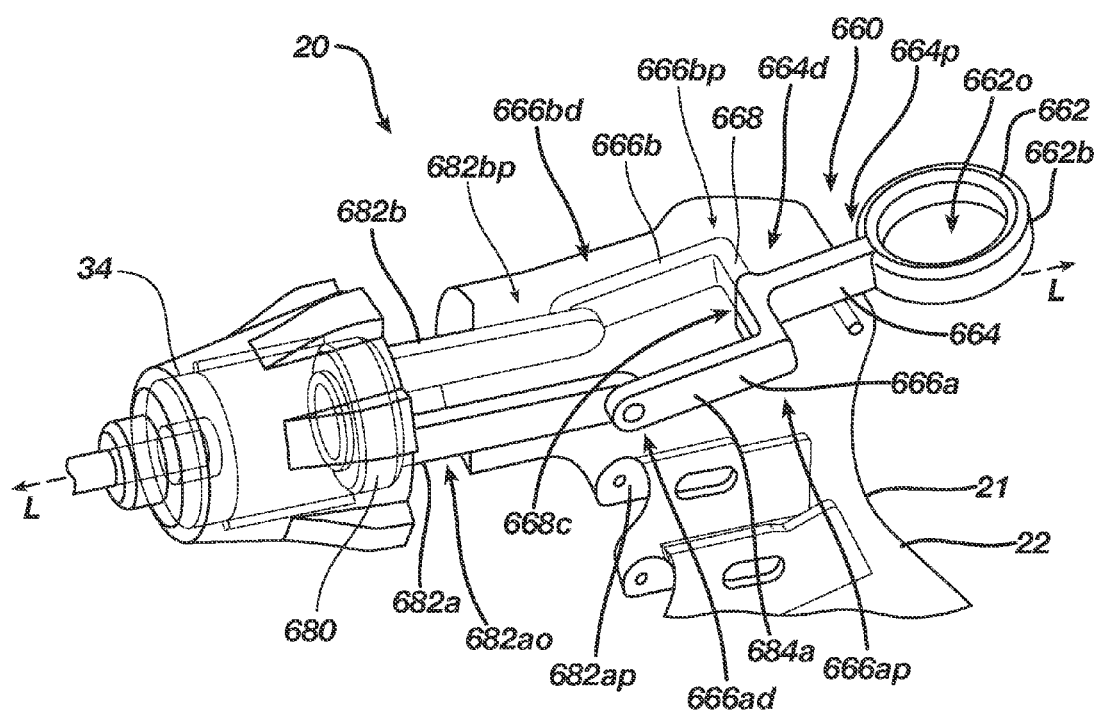
FIG. 14 is a semi-transparent perspective view of yet another exemplary embodiment of a handle portion and nozzle of a surgical device.
Figure 15A:
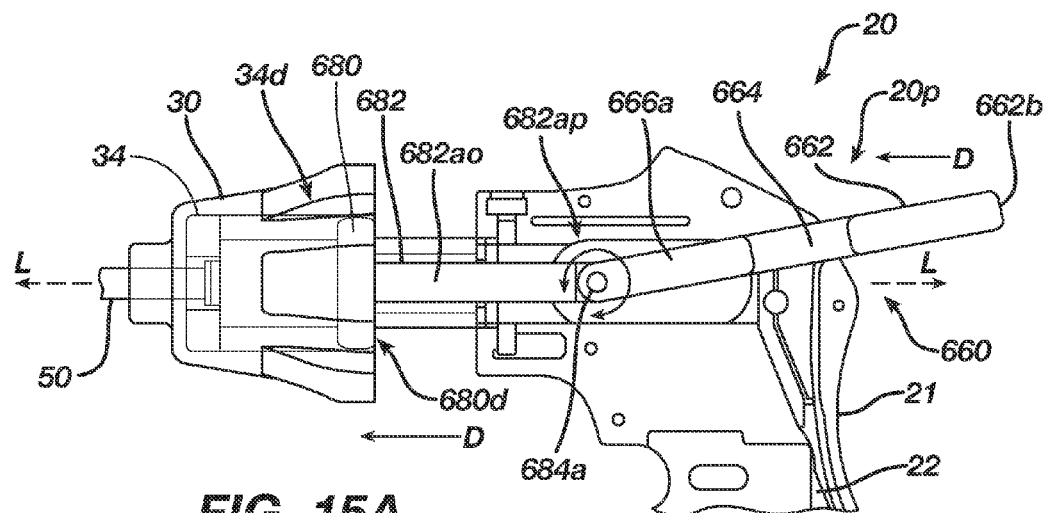
FIG. 15A is a semi-transparent side view of the handle portion and nozzle of FIG. 14 in which the nozzle is disposed in an extended position.
Figure 15B:
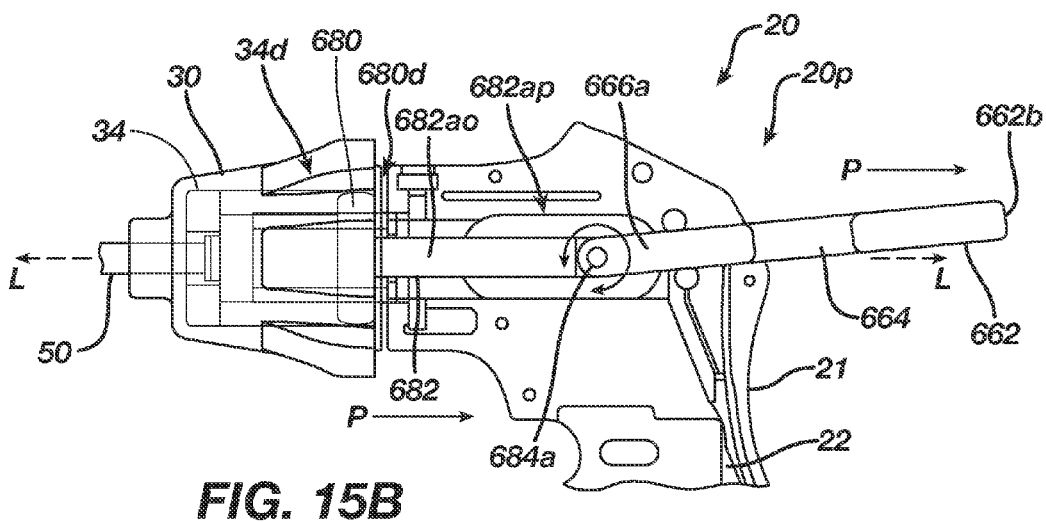
FIG. 15B is a semi-transparent side view of the handle portion and nozzle of FIG. 14 in which the nozzle is disposed in a retracted position.

The translating means illustrated in FIGS. 14, 15A, and 15B is a push-pull ring 660. As shown, the push-pull ring 660 includes a ring-shaped actuator 662 extending out of a back end 20*p* of the handle portion 20, with the ring 662 being coupled to a carrier 680. The carrier 680 is coupled to the nozzle 30 such that distal advancement and proximal retraction of the carrier 680 by way of the push-pull ring 660 is passed on to the nozzle 30, and thus the outer sheath 50.

The push-pull ring 660 can have a variety of configurations, but in the illustrated embodiment it includes the ring-shaped actuator 662, a first arm 664, two second arms 666a, 666b, and a frame bar 668. The ring-shaped actuator 662 has a substantially circular shape that defines an opening 662o for receiving a finger(s) or thumb of the user. The actuator 662 extends out of the housing 21 at a back or proximal end 20p of the handle portion 20 to allow a user to manipulate the ring 660 without adjusting a grip of the user's hand around the gripping section 22. Distal ends 666ad, 666bd of the second arms 666a, 666b are coupled to the carrier 680, and proximal ends 666ap, 666bp are connected to the frame bar 668. As shown, the proximal ends 666ap, 666bp are unitarily formed with the frame bar 668, although in other embodiments they can be separate components coupled to each other by any known manner for coupling two components together. The frame bar 668 is coupled to a distal end 664d of the first arm 664 at an approximate center 668c of the frame bar 668, and a proximal end 664p of the first arm 664 extends from a distal, central portion of the ring-shaped actuator 662. The balanced configuration of the switch 660 allows for movement imparted on the ring-shaped actuator 662 to be easily translated to the carrier 680, and thus to the nozzle 30 and outer sheath 50.

The carrier 680 can generally be configured to link the push-pull ring 660 with the nozzle 30. As shown, the carrier 680 has a ring-shaped distal end 680d that is configured to sit within the proximal portion 34p of the bore 34 of the nozzle 30, and is coupled to an inner wall of the nozzle that defines the proximal portion 34p of the bore 34. A diameter of the carrier 680 is generally complementary to a diameter of the distal rod 24 so that the carrier 680 can slide along a surface of the distal rod 24. The carrier 680 also includes two proximally-extending, opposed arms 682a, 682b that extend from the ring-shaped distal end 680d and towards the proximal end 20p of the handle portion 20. The arms can be substantially parallel to and disposed on opposite sides of the longitudinal axis L. The arms 682a, 682b can include a tab or pin 684a, 684b (not visible) formed on their respective proximal ends 682ap, 682bp to receive a bore formed on the respective distal ends 666ad, 666bd of the second arms 666a, 666b to form a pivotal connection therebetween. This pivotal connection allows the ring-shaped actuator 662 to pivot with respect to the carrier 680, providing some play between the two components, although the pivoting may be restricted by the configuration of the housing of the handle portion 20. As shown, the second arms 666a, 666b are disposed adjacent to outer surfaces 682ao, 682bo (not visible) of the arms 682a, 682b, although in other embodiments they can be disposed adjacent to inner surfaces. Further, in the illustrated embodiment, the arms 682a, 682b extend from a central section of the ring-shaped distal end 680d.

In use, a surgeon can push the ring-shaped actuator 662 in a distal direction D to slide the nozzle 30 distally along the distal rod 24 in the direction D, towards the distal end of the end effector, until the nozzle 30 reaches the extended position, as shown in FIG. 15A. The advancing movement of the nozzle 30 causes the distal end of outer sheath to also advance distally to its extended position and cover the distal end of the end effector. The surgeon can push the ring-shaped actuator 662 with a thumb or finger(s) of the same hand holding the gripping section 22 of the handle portion 20 without adjusting his or her grip on the gripping section 22, for instance by placing the thumb or finger in the opening 662o and pushing the wall adjacent to the first arm 664, or by placing the thumb or finger(s) on a back surface 662b of the ring-shaped actuator 662, outside of the opening 662o, and pushing the back surface 662b.

Likewise, a surgeon can pull the ring-shaped actuator 662 in a proximal direction P to slide the nozzle 30 proximally along the distal rod 24 in the direction P, towards the proximal end 20p of the handle portion 20, until the nozzle reaches the retracted position, as shown in FIG. 15B. The retracting movement of the nozzle 30 causes the distal end of the outer sheath to also retract proximally to its retracted position and exposes the distal end of the end effector. The surgeon can pull the ring-shaped actuator 662 with a thumb or finger(s) of the same hand holding the gripping section 22 of the handle portion 20 without adjusting his or her grip on the gripping section 22, for instance by placing the thumb of finger(s) in the opening 662o and pulling the wall adjacent to the back surface 662b.

Push-Pull Ring—Ring Distal of Gripping Section

Figure 16A:
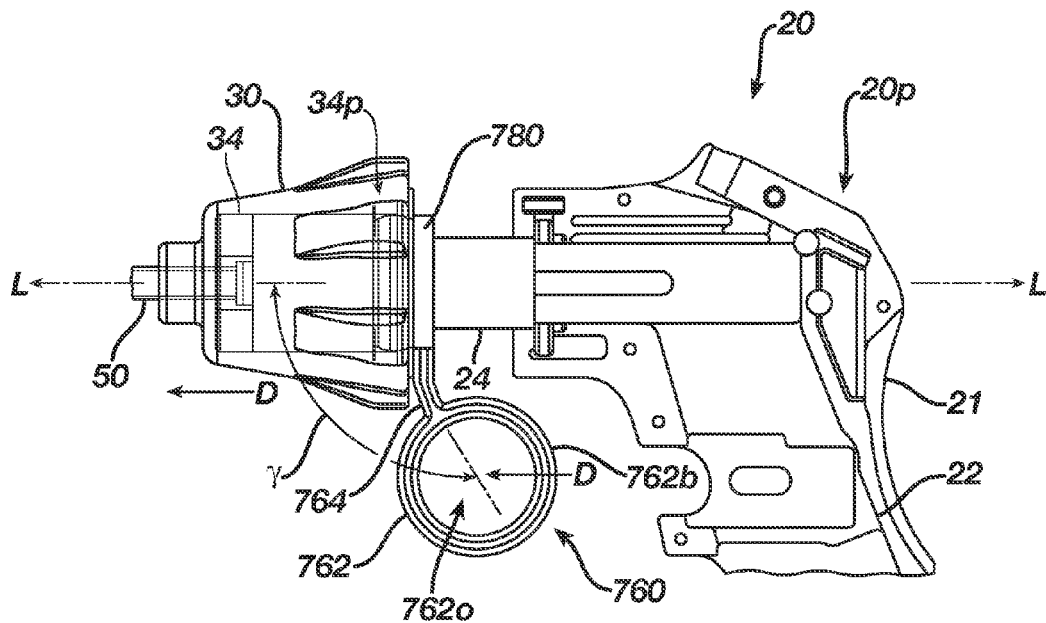
FIG. 16A is a semi-transparent side view of another exemplary embodiment of a handle portion and nozzle of a surgical device in which the nozzle is disposed in an extended position.
Figure 16B:
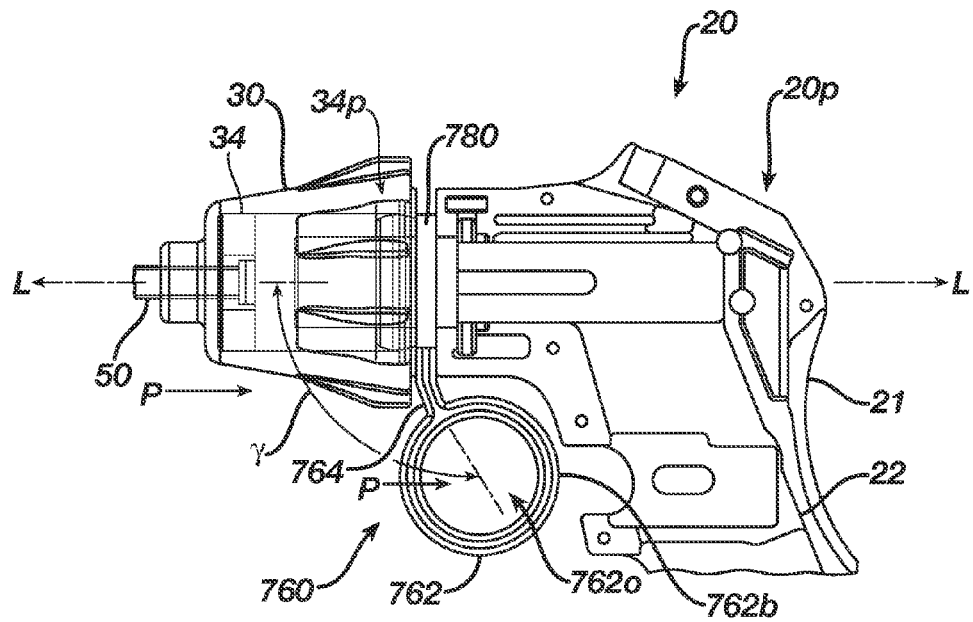
FIG. 16B is a semi-transparent side view of the handle portion and nozzle of FIG. 16B in which the nozzle is disposed in a retracted position.

The translating means illustrated in FIGS. 16A and 16B is another embodiment of a push-pull ring 760. As shown, the push-pull ring 760 includes a ring-shaped actuator 762 extending from and below a carrier 780. The carrier 780 is coupled to the nozzle 30 such that distal advancement and proximal retraction of the carrier 780 by way of the push-pull ring 760 is passed on to the nozzle 30, and thus the outer sheath 50.

As shown, the push-pull ring 760 includes a ring-shaped actuator 762 and an arm 764. The ring-shaped actuator 762 has a substantially circular shape that defines an opening 762o for receiving a finger(s) or thumb of the user. The actuator 762 extends out of the housing 21, below the distal rod 24 and distal of the gripping section 22 of the handle portion 20 to allow a user to manipulate the ring 760 without adjusting a grip of the user's hand around the gripping section 22. The arm 764 extends between the actuator 762 and the carrier 780. As shown, the arm can extend at an angle γ with respect to the longitudinal axis L that is greater than 90 degrees, thereby allowing forces applied to the actuator 762 to translate the carrier 780 along the distal rod 24.

The carrier 780 can generally be configured to link the push-pull ring 760 with the nozzle 30. As shown, the carrier 780 has a ring-shaped body that is configured to sit within the proximal portion 34p of the bore 34 of the nozzle 30, and is coupled to an inner wall of the nozzle that defines the proximal portion 34p of the bore 34. A diameter of the carrier 780 is generally complementary to a diameter of the distal rod 24 so that the carrier 780 can slide along a surface of the distal rod 24.

In use, a surgeon can push the ring-shaped actuator 762 in a distal direction D to slide the nozzle 30 distally along the distal rod 24, towards the distal end of the end effector, until the nozzle 30 reaches the extended position, as shown in FIG. 16A. The advancing movement of the nozzle 30 causes the distal end of outer sheath to also advance distally to its extended position and cover the distal end of the end effector. The surgeon can push the ring-shaped actuator 762 with a thumb or finger(s) of the same hand holding the gripping section 22 of the handle portion 20 without adjusting his or her grip on the gripping section 22, for instance by placing the thumb or finger in the opening 762o and pushing a distal-most wall, or by placing the thumb or finger(s) on a back surface 762b of the ring-shaped actuator 762, outside of the opening 762o, and pushing the back surface 762b.

Likewise, a surgeon can pull the ring-shaped actuator 762 in a proximal direction P to slide the nozzle 30 proximally along the distal rod 24, towards the proximal end 20p of the handle portion 20, until the nozzle reaches the retracted position, as shown in FIG. 16B. The retracting movement of the nozzle 30 causes the distal end of the outer sheath to also retract proximally to its retracted position and exposes the distal end of the end effector. The surgeon can pull the ring-shaped actuator 762 with a thumb or finger(s) of the same hand holding the gripping section 22 of the handle portion 20 without adjusting his or her grip on the gripping section 22, for instance by placing the thumb of finger(s) in the opening 762o and pulling the wall adjacent to the back surface 762b.

Figure 17:
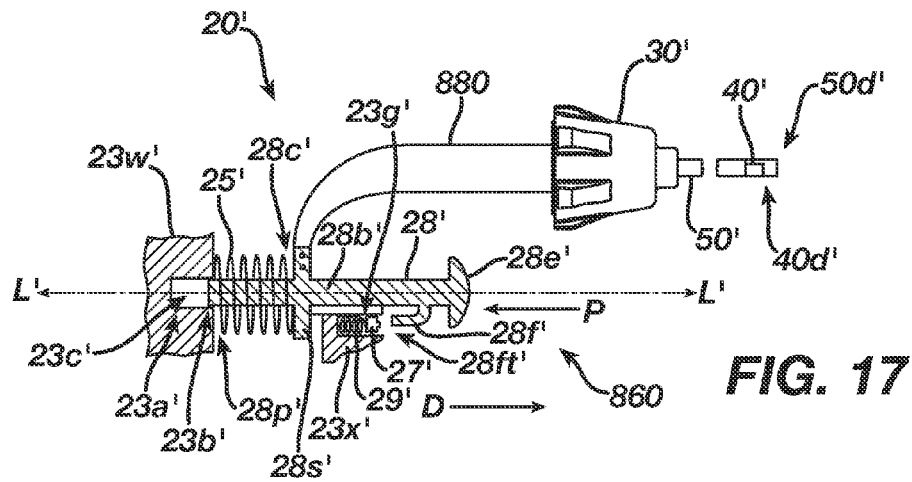
FIG. 17 is a schematic cross-sectional side view of one exemplary embodiment of components disposed in a handle portion of a surgical device, the components being configured to extend and retract an outer sheath of the surgical device and supply energy to an end effector of the device.

Button to Both Retract Outer Sheath and Apply Energy, Energy Application Prior to Full Retraction The translating means 860 illustrated in FIG. 17 is incorporated as part of a button 28' to deliver energy to an end effector 40'. Such a configuration allows a surgeon to both proximally retract an outer sheath 50' to expose a distal end 40d' of the end effector 40' and supply energy to the end effector 40' using the same component(s) of a handle portion 20' with his or her same hand, and even the same finger. A housing of the handle portion 20' in which the components illustrated can be situated is not shown to allow for the other components to be easily viewed. A person skilled in the art will understand that the housing can be similar to the housing 21 of the handle portion 20, or can be a housing that is shaped, sized, and configured to accommodate the illustrated components. Further, also for illustrative purposes to highlight the components of the translating means 860, the figure is not to scale. Similar to the other translating means disclosed herein, because the translating means 860 is incorporated as part of the button 28' that delivers energy to the end effector 40', the translating means 860 can be operated by the hand of a user from the same location on the gripping section of the handle portion as the hand is located when positioning the device and when applying energy to the end effector.

The button 28' includes an elongate bar 28b' with an end cap 28e' disposed at a distal end 28d' thereof, a proximal end 28p' that is associated with a first wall 23w' of the housing, and a coupling mechanism 28c' disposed along an intermediate length of the bar 28b' such that proximal and distal movement of the bar 28b' results in respective proximal and distal movement of the outer sheath 50'. The proximal end 28p' is associated with a channel 23c' formed in the first wall 23w' to allow for translation of the bar 28b' between two ends 23a', 23b' of the channel 23c'. The bar 28b' can be associated with the channel 23c' so that it is unable to slide out of the channel 23c' using any number of techniques known to those skilled in the art.

As shown, the coupling mechanism 28c' is in the form of a second bar 28s', extending substantially perpendicular a longitudinal axis L' of the bar 28b'. The second bar 28s' is coupled to a carrier 880, which is coupled to a nozzle 30' such that distal advancement and proximal retraction of the carrier 880 by way of the first and second bars 28b', 28s' is passed on to the nozzle 30', and thus the outer sheath 50'. The carrier 880 is only schematically illustrated herein, and in practice it can take a configuration similar to the configurations of other carriers provided for herein or otherwise derivable from the present disclosures and knowledge of those skilled in the art. A spring 25' can be disposed around the bar 28b' between the first wall 23w' and the second bar 28s', providing increased resistance as the elongate bar 28b' retracts proximally in a direction P, and providing a return force when a force in the direction P is not being applied.

The button 28' further includes a switch engagement extension 28f', located proximal of the end cap 28e'. The switch engagement extension 28f' includes a terminal end 28ft' that is configured to translate proximally and distally parallel to and at the same time as the elongate bar 28b'. The terminal end 28ft' can be configured to engage an energy activation switch 27' disposed in a second channel 23g' formed in a second wall 23x' of the housing of the handle portion 20'. The switch 27' can be associated with the channel 23g' so that it is unable to slide out of the channel 23g' using any number of techniques known to those skilled in the art. A spring 29' can be disposed proximal of the energy activation switch 27', between the switch 27' and the second wall 23x'. The spring 29' can generally be stiffer than the spring 25'.

In use, a surgeon pushes the end cap 28e' of the button 28' in the proximal direction P to slide the bar 28b' proximally into the channel 23c'. As the bar 28b' retracts proximally, so too does the coupling mechanism 28c', which in turn compresses the spring 25'. Once the bar 28b' engages the terminal end 23a' of the channel 23c', further proximal movement of the bar 28b', and thus the coupling mechanism 28c', ceases and the spring 25' remains under the compression force supplied by the coupling mechanism 28c'. As the bar 28b' retracts proximally to its retracted position, the nozzle 30' and the outer sheath 50' also both retract in the direction P to their respective retracted positions. The distal end 40d' of the end effector 40' is exposed by the outer sheath 50' when the bar 28b', nozzle 30', and outer sheath 50' are in their retracted positions.

As bar 28b' retracts proximally, so too does the extension 28f'. As the extension 28f' retracts proximally in the direction P, it engages the energy activation switch 27' to turn on the energy source and supply energy to the end effector 40'. As shown, the distance between the two ends 23a', 23b' of the channel 23c' in which the bar 28b' travels is greater than the initial distance between the terminal end 28ft' and the energy activation switch 27', and thus the terminal end 28ft' engages the activation switch 27' prior to the bar 28b' reaching its retracted position in which it engages the terminal end 23a'. The stiffness of the spring 29' is such that the terminal end 28ft' can activate the switch 27' upon engagement, and then further force applied by the surgeon to the end cap 28e' can cause the switch 27' and extension 28f' to retract proximally, compressing the spring 29' between the switch 27' and the second wall 23x'. The configuration of the extension 28f', switch 27', and spring 29' allows energy to be supplied to the end effector 40' prior to the outer sheath 50' reaching its fully retracted position. This can be useful, for example, in instances in which a surgeon merely wants to touch-up an area being treated, and thus does not need to wait to apply the energy until the outer sheath 50' is in the retracted position. In alternative embodiments, the spring 29' can be eliminated, and the spacing between the terminal end 28ft' of the extension 28f' and the activation switch 27' can be similar to the distance between the two ends 23a', 23b' of the channel 23c', i.e., the distance the bar 28b' travels to reach the retracted position. Such a configuration would activate the switch 27' and supply energy to the end effector 40' approximately at the same time the bar 28b', nozzle 30', and outer sheath 50' reached the retracted position.

When a surgeon releases the button 28' and thus no longer supplies force in the proximal direction P, each of the bar 28b', carrier 880, nozzle 30', and outer sheath 50' can advance distally in a direction D so that the distal end 50d' of the outer sheath 50' covers the distal end 40d' of the end effector 40'. Likewise, the switch 27' and the extension 25f' also advance distally in the direction D, with the extension 25f' coming out of contact with the switch 27' so that energy is no longer supplied to the end effector 40'.

Button to Both Retract Outer Sheath and Apply Energy

Figure 18A:
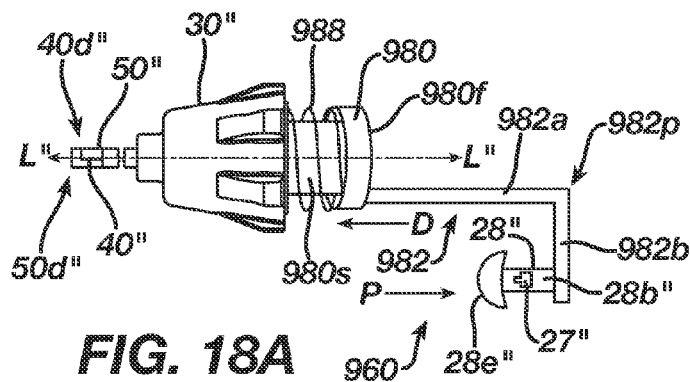
FIG. 18A is a schematic cross-sectional side view of another exemplary embodiment of components disposed in a handle portion of a surgical device, the components being configured to extend and retract an outer sheath of the surgical device and supply energy to an end effector of the device.

Similar to the translating means 860, the translating means 960 illustrated in FIG. 18A is also incorporated as part of a button 28" to deliver energy to an end effector 40", thus allowing the surgeon to both retract an outer sheath 50" and supply energy to the end effector 40" using the same component(s) of a handle portion 20" with his or her same hand, and even the same finger. The housing of the handle portion 20" in which the components illustrated can be situated is again not shown to allow for the other components to be easily viewed, although a person skilled in the art will understand a variety of different configurations that the housing can have to accommodate the illustrated components. Further, also for illustrative purposes to highlight the components of the translating means 960, the figure is not to scale. Like the other translating means disclosed herein, the translating means 960 can be operated by the hand of a user from the same location on the gripping section of the handle portion as the hand is located when positioning the device and when applying energy to the end effector.

The button 28" includes an end cap 28e" and a shroud-mounted energy activation switch 27" disposed proximal of the end cap 28e" within a shaft 28b" of the button 28". The shaft 28b" can be coupled to a carrier 980, which is coupled to a nozzle 30" such that distal advancement and proximal retraction of the carrier 980 by way of the button 28" is passed on to the nozzle 30", and thus the outer sheath 50". The carrier 980 can be configured to couple to the nozzle 30" using techniques described herein with respect to other embodiments or using other techniques known to those skilled in the art. In the illustrated embodiment, the carrier 980 includes a ring-shaped body having a flange 980f and a shaft 980s extending distally from the flange 980f. A return spring 988 can be disposed around the shaft 980s. The carrier 980 can also include a proximally extending arm 982 that extends from a bottom portion of the flange 980f and towards a proximal end of a handle portion. In the illustrated embodiment, the arm 982 has a portion 982a that extends proximally, substantially parallel to a longitudinal axis L" of the outer sheath 50", and then a portion 982b that extends downward, substantially perpendicular to the longitudinal axis L" at a proximal end 982p of the arm 982. In the illustrated embodiment, the button 28" is mounted to the portion 982b, although a person skilled in the art will recognize a number of other configurations that can be used without departing from the spirit of the present disclosure.

In use, a surgeon pushes the end cap 28e" of the button 28" in a proximal direction P to slide the carrier 980, and thus the nozzle 30" and outer sheath 50", proximally towards the handle portion 20". The proximal retraction in the direction P of the nozzle 30" and outer sheath 50" to the respective retracted positions exposes the distal end 40d" of the end effector 40". In the illustrated embodiment, once the retracted positions of the nozzle 30" and outer sheath 50" are reached, then the end cap 28e" can engage the switch 27" to initiate energy delivery to the end effector 40". The delivery of energy can occur using any number of techniques known to those skilled in the art, including but not limited to actuation of the switch 27" completing a circuit to begin energy flow or the switch supplying a radio frequency signal to complete a circuit at some other location in the device to begin energy flow.

After the energy has been delivered, a surgeon releases the button 28" and thus a force in the proximal direction P is no longer supplied. As a result, each of the button 28", carrier 980, nozzle 30", and outer sheath 50" can advance distally in a direction D so that the distal end 50d" of the outer sheath 50" covers the distal end 40d" of the end effector 40".

Two Buttons to Separate Cutting and Coagulation Functions

Figure 18B:
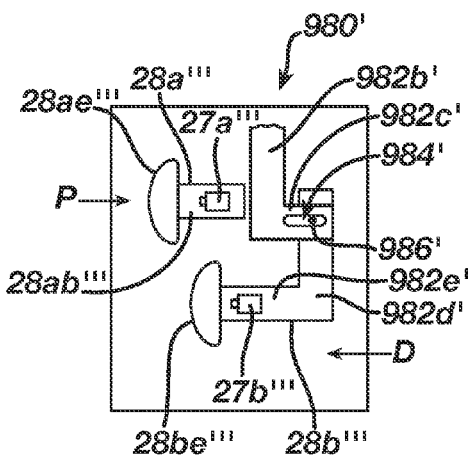
FIG. 18B is a schematic cross-sectional side view of one exemplary embodiment of a button configuration for performing two different functions with the surgical device of FIG. 18A.

FIG. 18B provides for a modified version of buttons to be used as part of the translating means 980. As shown, rather than using a single button 28" to perform all of the energy tasks, e.g., cutting and coagulating, the buttons 28a''', 28b''' are configured so that one button performs one task and the other button performs the other task.

In the illustrated embodiment, the first button 28a''' is configured to be removably attached to a second portion 982b' of a carrier 980' such that the first button 28a''' extends distally from the second portion 982b'. Included within a shaft 28ab''' of the button 28a''' is a shroud-mounted energy activation switch 27a''', disposed proximal of an end cap 28ae''' of the button 28a'''. The second portion 982b' then extends downwardly to a third portion 982c' that is substantially perpendicular to the second portion 982b', substantially parallel to the first portion 982a' (not shown), and extends proximally from the second portion 982b'. As shown, a channel 984' is formed in the third portion 982c'. The channel 984' receives a pin 986' associated with a fourth portion 982d' of the carrier 980'.

The fourth portion 982d' is formed separate from the first, second, and third portions 982a', 982b', 982c', but is coupled to the third portion 982c' by way of the pin 986' and channel 984'. As shown, the fourth portion 982d' extends downward, substantially perpendicular to the third portion 982c', and substantially parallel to the second portion 982b'. A fifth portion 982e' extends distally, substantially perpendicular to the fourth portion 982d', and substantially parallel to the third portion 982c'. The fifth portion 982e' can also serve as a shaft of the second button 28b''', and can include a shroud-mounted energy activation switch 27b''' disposed proximal of an end cap 28be''' of the button 28b'''. In this configuration, the first button 28a''' can be used to perform cutting, while the second button 28b''' can be used to perform coagulating, or vice versa. Other functionalities related to supplying energy can also be associated with either of the buttons 28a''', 28b'''.

Figure 18C:
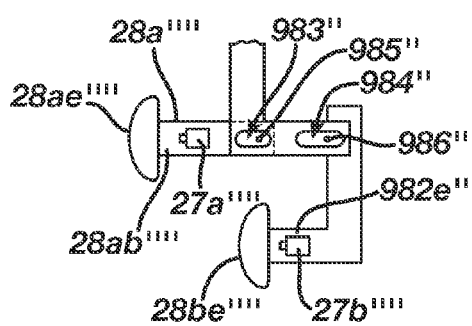
FIG. 18C is a schematic cross-sectional side view of another exemplary embodiment of a button configuration for performing two different functions with the surgical device of FIG. 18A.

In an alternative embodiment, the button 28a''' is not attached to the carrier 980', but is instead slidably engaged to the housing of the instrument such that the button 28a''' can move the carrier 980' when the button 28a''' is depressed by the surgeon, but the button 28a''' is not moved when the button 28b''' is actuated. In still further embodiments, for instance as shown in FIG. 18C, a button 28a'''' can be coupled to a carrier by way of a channel 983" and pin 985", similar to the channel 984' and pin 986' configuration used for the button 28b''' in FIG. 18B, and as also provided for in FIG. 18C as channel 984" and pin 986". As shown in FIG. 18C, switches 27a'''' and 27b'''' can be provided within shafts 28ab'''', 982e" of the translating means, and end caps 28ae'''', 28be'''' can be provided for the surgeon to depress, which in turn can activate the respective switches 27a'''', 27b''''.

Turning back to FIG. 18B, in use, a surgeon grabs a hold of the device, which typically has the button 28a''' attached to the second portion 982b' during manufacturing. The surgeon pushes the end cap 28ae''' of the button 28a''' in a proximal direction P (or continues to push the end cap 28ae''' in that direction if attaching the button 28a''' involved pushing the end cap 28ae''' in the proximal direction P) to slide the carrier 980', and thus the nozzle and outer sheath, proximally towards a handle portion. The proximal retraction of the nozzle and outer sheath in the direction P to the respective retracted positions exposes the distal end of the end effector. Further, in the illustrated embodiment, once the retracted positions of the nozzle and outer sheath (not shown) are reached, then the end cap 28ae''' can engage the switch 27a''' to initiate energy delivery to the end effector to perform cutting at the surgical site. The delivery of energy can occur using any number of techniques known to those skilled in the art, including but not limited to actuation of the switch 27a''' completing a circuit to begin energy flow or the switch 27a''' supplying a radio frequency signal to complete a circuit at some other location in the device to begin energy flow. Notably, because of the configuration of the first and second buttons 28a''' and 28b''', application of a force in the proximal direction P to the button 28a''' does not activate the coagulation functionality of the button 28b'''.

A surgeon that then wants to perform a coagulation function can push the end cap 28be''' of the button 28b''' in the proximal direction P. This allows the end cap 28be''' to engage the switch 27b''' to initiate delivering energy to the end effector to perform coagulation at the surgical site. Similar to the switch 27a''', the energy delivery can occur using any number of techniques known to those skilled in the art, including but not limited to actuation of the switch 27b''' completing a circuit to begin energy flow or the switch supplying a radio frequency signal to complete a circuit at some other location in the device to begin energy flow. Further, because of the configuration of the first and second buttons 28a''' and 28b''', application of a force in the proximal direction P to the button 28b''' does not activate the cutting functionality of the button 28a'''.

After the energy has been delivered, a surgeon releases whichever button 28a''', 28b''' he or she was most recently using, and thus a force in the proximal direction P is no longer applied to either of the buttons 28a''', 28b'''. As a result, each of the button 28a''', button 28b''', carrier 980', nozzle, and outer sheath can advance distally in a direction D so that the distal end of the outer sheath covers the distal end of the end effector.

The shapes, sizes, and configurations of the various translating means and related components can depend on a variety of factors, including but not limited to the shapes, sizes, and configurations of the other components of the device, the type of procedure being performed, and the anatomy of the patient. Generally, the translating means and related components are sized to fit within a housing of the handle portion and/or extend reasonably therefrom as described herein. Further, any number of materials can be used to form the various components of the disclosed translating means. Various metals or polymers can be used, including but not limited to polyoxymethylene copolymer (POM), polyamides, polycarbonate, polyetherimide, polyetheretherketone, polyethylene, polylactic acid/polylactide acid (PLA), polypropylene, polystyrene, polyurethane, polyvinyl chloride (PVC), thermoplastic elastomer, stainless steel, cobalt-chromium based alloys, titanium, aluminum, and nickel alloys.

Surgical Procedure

In one exemplary embodiment of a surgical procedure using the device 10 of FIGS. 1A and 1B, a surgeon can grip the handle portion 20 by placing the gripping section 22 in the palm of the surgeon's hands and wrapping the surgeon's fingers and thumbs around the gripping section 22 to establish a gripping position for the hand. The surgeon can then guide the device 10 to the surgical site. For example, the surgeon can maintain his or her hold on the gripping section 22 and manipulate the distal ends 40d and 50d of the end effector 40 and outer sheath 50 to the desired location. During such movement, the distal end 50d of the outer sheath 50 can cover the distal end 40d of the end effector 40 to shield tissue and other components from coming into contact with the end effector 40, which in some embodiments can include a pointed distal end, or a distal end that is not in-line with a shaft of the end effector.

Once the distal ends 40d, 50d are positioned within the vicinity of the surgical site, a number of functions can be performed by the surgeon, each of which can be performed by the surgeon without the surgeon having to adjust a location of his or her hand on the gripping section 22 of the device 20 to activate the desired functionality. For example, if the surgeon wants to irrigate or suction the surgical site, the surgeon can keep the distal end 50d of the outer sheath 50 over the distal end 40d of the end effector 40 and press the respective buttons configured to deliver fluid or a suction force to the surgical site via the outer sheath 50. If the surgeon wants to transect or coagulate tissue at the surgical site, then the surgeon can retract the distal end 50d of the outer sheath 50 to expose the distal end 40d of the end effector 40 and then apply energy to the end effector 40. Any of the translating means provided for herein or otherwise derivable from the present disclosures can be used to retract, and later advance, the outer sheath 50. All such transecting means are configured in a manner that allows the surgeon to operate the translating means with the hand holding the gripping section 22 of the handle portion 20 without having to adjust a location or position of the hand with respect to the gripping section 22. With respect to the illustrated embodiment, the surgeon operates the switch 60 by pushing the proximal-most linkage 62p in the second direction K to retract the carrier 80, nozzle 30, and outer sheath 50. This, in turn, exposes the distal end 40p of the end effector 40.

Energy can be applied to the end effector. In the illustrated embodiment, this involves pushing the button 28 to initiate application of the energy. The energy can be applied after the outer sheath 50 has reached the retracted position, or alternatively, the energy can be applied prior to the outer sheath 50 reaching the retracted position, in accordance with the disclosures provided for herein. The energy can be supplied to transect or cut tissue, coagulate tissue, or do both. Once the desired result is achieved, the energy application can be stopped, for instance by releasing the button 28.

The switch 60 can now be operated to return the carrier 80, nozzle 30, and outer sheath 50 to the extended positions such that the distal end 50d of the outer sheath 50 covers the distal end 40d of the end effector 40. The surgeon can push the proximal-most linkage member 62 of the switch 60 in the first direction J to advance the nozzle 30 to the extended position. Again, the switch 60 can be operated by the surgeon using the hand holding the gripping section 22 of the handle portion 20 without having to adjust a location or position of the hand with respect to the gripping section 22. If additional irrigation or suction is desired, the surgeon can perform such procedures using the device 10 as described. A person skilled in the art will recognize that the steps of applying energy, providing irrigation, and providing suction, can be mixed and matched during the course of the surgical procedure to achieve desired results. Thus, the translating means provided for herein allow for a surgeon to easily advance and retract the outer sheath 50 to selectively expose and cover the end effector 40 during these various steps without having to adjust the surgeon's grip or location of the surgeon's hand on the handle portion. Once the surgeon is ready to remove the device 10 from the surgical site, the surgeon can maintain the same grip on the gripping section 22 he or she has had throughout the surgical procedure and guide the end effector 40 and the outer sheath 50 away from the surgical site.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. By way of non-limiting examples, the embodiments of FIGS. 17-18B that relate to using the same button to actuate the nozzle and outer sheath and supply energy to the end effector can be combined with other forms of translating means provided for herein such that any of the translating means disclosed can be adapted to also initiate applying energy to the end effector. All publications and references cited herein are expressly incorporated herein by reference in their entirety.

What is claimed is:

1. A surgical device, comprising:
an end effector having a proximal end, a distal end, and an elongate shaft extending between the proximal and distal ends, the distal end being configured to deliver energy;
a cannulated outer sheath having a proximal end, a distal end, and an intermediate length extending between the proximal and distal ends, the end effector being disposed within the outer sheath, and the distal end having a plurality of holes formed in an outer surface thereof, the holes being in fluid communication with the remainder of the cannulated outer sheath to provide at least one of suction and irrigation to a surgical site;
a nozzle coupled to the proximal end of the outer sheath and configured to translate along a longitudinal axis of the cannulated outer sheath;
a carrier coupled to the nozzle;
a handle portion coupled to the proximal end of the end effector, the handle portion having a switch,
wherein the carrier is coupled to the switch such that operation of the switch distally advances the carrier to distally advance the nozzle with respect to the handle portion to selectively cover the distal end of the end effector with the distal end of the outer sheath, and operation of the switch proximally retracts the carrier to proximally retract the nozzle with respect to the handle portion to selectively expose the distal end of the end effector.

2. The device of claim 1, wherein the handle portion comprises a pistol grip.

3. The device of claim 1, further comprising:
a plurality of segments including a distal-most segment and a proximal-most segment, the distal-most segment being coupled to the carrier, and a proximal end of the proximal-most segment extending proximally away from a back end of the handle portion,
wherein the switch is configured to distally advance the carrier with respect to the handle portion in response to an extension force applied to the proximal-most segment in a direction substantially perpendicular to the longitudinal axis of the outer sheath, and proximally retract the carrier with respect to the handle portion in response to a retraction force applied to the proximal-most segment in a direction approximately opposite to the direction of the extension force.

4. The device of claim 1, further comprising:
a plurality of linkages including two distal-most linkages and a proximal-most linkage, the two distal-most linkages being coupled to opposed sides of the carrier, a proximal end of the proximal-most linkage extending outside of a housing of the handle portion, and the proximal-most linkage being configured to rotate about a pivot point of the plurality of linkages,
wherein the switch is configured to distally advance the carrier with respect to the handle portion in response to an extension force applied to the proximal-most linkage to rotate the proximal-most linkage about the pivot point in a first direction, and proximally retract the carrier with respect to the handle portion in response to a retraction force applied to the proximal-most linkage to rotate the proximal-most linkage about the pivot point in a second direction that is opposite of the first direction.

5. The device of claim 1, further comprising:
a tab disposed on a proximal portion of the carrier; and
a translating arm having a distal end that is rotatably coupled to a housing of the handle portion, an intermediate portion that includes an elongate channel formed therein, the tab of the carrier being disposed in the elongate channel to translate therein, and a proximal end extending outside of a housing of the handle portion,
wherein the switch is configured to distally advance the carrier with respect to the handle portion in response to an extension force applied to the proximal end of the translating arm in a direction substantially perpendicular to the longitudinal axis of the outer sheath, and proximally retract the carrier with respect to the handle portion in response to a retraction force applied to the proximal end of the translating arm in a direction approximately opposite to the direction of the extension force.

6. The device of claim 1, further comprising:
a tab disposed on a proximal portion of the carrier; and
a slider having an elongate channel formed therein, the tab of the carrier being disposed in the elongate channel to translate therein, and first and second arms disposed on opposed sides of an intermediate portion of the length of the elongate channel, the elongate channel being disposed at an angle with respect to the longitudinal axis of the outer sheath such that an angle extending between a distal end of the elongate channel and the longitudinal axis of the outer sheath is an acute angle,
wherein the switch is configured to distally advance the carrier with respect to the handle portion in response to an extension force applied to the first arm in a direction substantially perpendicular the longitudinal axis of the outer sheath, and proximally retract the carrier with respect to the handle portion in response to a retraction force applied to the second arm in a direction approximately opposite to the direction of the extension force.

7. The device of claim 1, further comprising:
a slider tab coupled to a proximal end of the carrier, the slider tab extending outside of a top end of the handle portion,
wherein the switch is configured to distally advance the carrier with respect to the handle portion in response to an extension force applied to the slider tab in a direction substantially parallel to the longitudinal axis of the outer sheath, and to proximally retract the carrier with respect to the stationary handle in response to a retraction force applied to the slider tab in a direction approximately opposite to the direction of the extension force.

8. The device of claim 1, wherein the switch is further configured to selectively apply energy to the end effector.

9. A surgical device, comprising:
a handle portion;
an end effector extending distally from the handle portion and having a distal end configured to deliver energy;
an outer sheath extending distally from the handle portion, the outer sheath having a through-hole extending a length thereof with the end effector being disposed therein, the outer sheath being configured to distally advance and proximally retract to selectively cover and expose the distal end of the end effector;
a nozzle engaged with the outer sheath and configured to distally advance and proximally retract the outer sheath with respect to the distal end of the end effector upon distal advancement or proximal retraction of nozzle;
a carrier engaged with the nozzle and configured to distally advance and proximally retract the nozzle upon distal advancement or proximal retraction of the carrier; and
a translator engaged with the carrier, the translator configured to distally advance and proximally retract the carrier, the translator being associated with the handle portion and configured to be manually operated to advance or retract the carrier.

10. The surgical device of claim 9, wherein the handle portion comprises a pistol grip on which the user's hand is configured to be disposed when the user operates the translator, positions the device, and applies energy to the end effector.

11. The surgical device of claim 9, wherein the translator includes one of a switch, a thumbwheel, a push-pull ring, and a button configured to both retract the carrier and apply energy to the end effector.

12. The surgical device of claim 9, wherein the carrier disposed within and coupled to a housing of the nozzle.

13. The surgical device of claim 9, wherein the translator is further configured to selectively apply energy to the end effector.

14. The device of claim 1, wherein the switch includes a button that is operable to both: (1) advance and retract the carrier; and (2) selectively apply energy to the monopolar end effector.

15. The device of claim 1, wherein the switch includes a first button that is operable to advance and retract the carrier and to apply energy to the monopolar end effector at a first level, and a second button that is operable to advance and retract the carrier and to apply energy to the monopolar end effector at a second level that is different from the first level, the first and second buttons being coupled to a common shaft and being independently operable from the other.

16. The device of 9, wherein the translator includes a button that is operable to both: (1) advance and retract the carrier; and (2) selectively apply energy to the end effector.

17. The device of claim 9, wherein the translator includes a first button that is operable to advance and retract the carrier and to apply energy to the end effector at a first level, and a second button that is operable to advance and retract the carrier and to apply energy to the end effector at a second level that is different from the first level, the first and second buttons being coupled to a common shaft and being independently operable from the other.

18. The device of claim 1, wherein the end effector is monopolar.

19. The device of claim 1, wherein the cannulated outer sheath is insulating.

20. The surgical device of claim 9, wherein the translator is configured to be operated with a user's hand disposed on the handle portion without the user having to adjust a location of the user's hand from a location at which the hand is disposed when positioning the device and applying energy to the end effector.

* * * * *